(12) United States Patent
Vrudhula et al.

(10) Patent No.: US 9,708,337 B2
(45) Date of Patent: Jul. 18, 2017

(54) ARYL AMIDE-BASED KINASE INHIBITORS

(71) Applicant: Bristol-Myers Squibb Company, Princeton, NJ (US)

(72) Inventors: Vivekananda M. Vrudhula, Killingworth, CT (US); Carolyn Diane Dzierba, Middletown, CT (US); Joanne J. Bronson, Durham, CT (US); John E. Macor, Washington Crossing, PA (US); Susheel Jethanand Nara, Mumbai (IN); Ramkumar Rajamani, Woodbridge, CT (US); Maheswaran Sivasamban Karatholuvhu, Chennai (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 6 days.

(21) Appl. No.: 14/767,952

(22) PCT Filed: Feb. 6, 2014

(86) PCT No.: PCT/US2014/015120
§ 371 (c)(1),
(2) Date: Aug. 14, 2015

(87) PCT Pub. No.: WO2014/130258
PCT Pub. Date: Aug. 28, 2014

(65) Prior Publication Data
US 2016/0016967 A1    Jan. 21, 2016

Related U.S. Application Data

(60) Provisional application No. 61/768,051, filed on Feb. 22, 2013.

(51) Int. Cl.
*C07D 491/052* (2006.01)
*A61K 31/436* (2006.01)

(52) U.S. Cl.
CPC ................. *C07D 491/052* (2013.01)

(58) Field of Classification Search
CPC ................ C07D 491/052; A61K 31/436
USPC ............................................. 546/89; 514/290
See application file for complete search history.

(56) References Cited

U.S. PATENT DOCUMENTS

| | | |
|---|---|---|
| 8,946,415 B2 | 2/2015 | Bi et al. |
| 8,969,565 B2 | 3/2015 | Bi et al. |
| 2014/0080834 A1 | 3/2014 | Lanthorn et al. |

FOREIGN PATENT DOCUMENTS

| | | |
|---|---|---|
| CN | 1733708 A | 2/2006 |
| JP | 2007-217408 A | 8/2007 |
| WO | WO 94/12461 A1 | 6/1994 |
| WO | WO 96/21464 A1 | 7/1996 |
| WO | WO 03/086325 A2 | 10/2003 |
| WO | WO 2004/056745 A2 | 7/2004 |
| WO | WO 2004/072018 A1 | 8/2004 |
| WO | WO 2005/000309 A2 | 1/2005 |
| WO | WO 2006/012227 A2 | 2/2006 |
| WO | WO 2007/117715 A2 | 10/2007 |
| WO | WO 2008/022154 A2 | 2/2008 |
| WO | WO 2013/134036 A1 | 9/2013 |
| WO | WO 2014/022167 A1 | 2/2014 |
| WO | WO 2015/002915 A1 | 1/2015 |
| WO | WO 2015/002926 A1 | 1/2015 |
| WO | WO 2015/038112 A1 | 3/2015 |
| WO | WO 2015/116060 A1 | 8/2015 |

OTHER PUBLICATIONS

Buonanno, A., "The neuregulin signaling pathway and schizophrenia: From genes to synapses and neural circuits", Brain Research Bulletin, vol. 83, pp. 122-131 (2010).
Conner, S.D. et al., "AAK1-Mediated μ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia from the Consortium on the Genetics of Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor μ2 kinase", The Journal of Cell Biology, vol. 163, No. 2, pp. 231-236 (2003).

(Continued)

*Primary Examiner* — Rita Desai
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

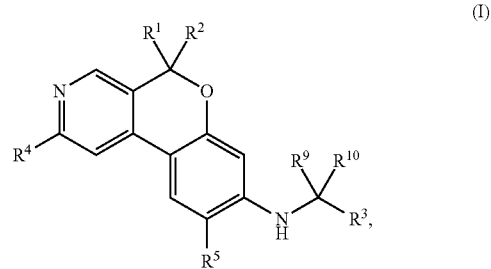

10 Claims, No Drawings

(56) References Cited

OTHER PUBLICATIONS

Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", BMC Medical Genetics, vol. 10 (2009), doi:10.1186/1471-2350-10-98.
Motley, A.M. et al., "Functional Analysis of AP-2 $\alpha$ and $\mu$2 Subunits", Molecular Biology of the Cell, vol. 17, pp. 5298-5308 (2006).
Ricotta, D. et al., "Phosphorylation of the AP2 $\mu$ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci., vol. 107, No. 3, pp. 1211-1216 (2010).

ARYL AMIDE-BASED KINASE INHIBITORS

This application claims priority to U.S. Provisional Patent Application Ser. No. 61/768,051, filed Feb. 22, 2013, which is incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA*. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In a first aspect the present disclosure provides a compound of formula (I)

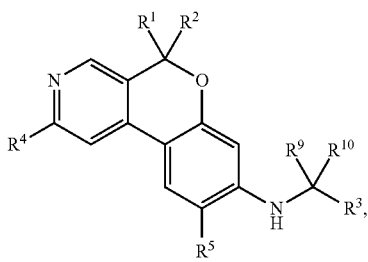

(I)

or a pharmaceutically acceptable salt thereof, wherein:

$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or $R^1$ and $R^2$ together are oxo;

$R^3$ is selected from $C_1$-$C_6$alkoxy, $C_2$-$C_6$alkynyl, amino, $C_3$-$C_6$cycloalkyl optionally substituted with $C_1$-$C_3$alkyl or cyano, $C_3$-$C_6$cycloalkylamino, piperidinyl optionally substituted with $C_1$-$C_6$alkyl, $C_1$-$C_3$alkyl-Y, and $C_1$-$C_8$alkyl, wherein the $C_1$-$C_8$alkyl is optionally substituted with one, two, or three groups independently selected from $C_1$-$C_3$alkoxy, $C_1$-$C_3$alkylamino, $C_1$-$C_3$alkoxy$C_2$-$C_3$alkylamino, $C_1$-$C_3$alkoxycarbonyl, amino, aminosulfonyl, aryl, cyano, $C_1$-$C_3$dialkylamino, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, and hydroxy;

$R^5$ is selected from hydrogen, $C_1$-$C_3$alkyl, cyano, $C_3$cycloalkyl, and halo;

$R^x$ and $R^y$, together with the nitrogen atom to which they are attached, form a three- to six-member ring optionally substituted with oxo; and Y is selected from

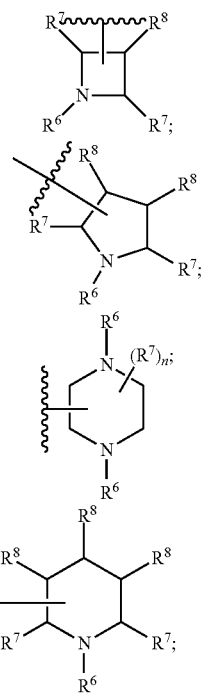

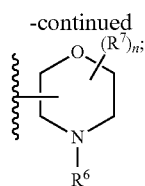

wherein $R^6$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^7$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl;

each $R^8$ is independently selected from hydrogen, $C_1$-$C_3$alkoxy and hydroxy; and $R^9$ and $R^{10}$ are each hydrogen or together form an oxo group.

In a first embodiment of the first aspect the present disclosure provides a compound of formula (I), or a pharmaceutically acceptable salt thereof, wherein $R^9$ and $R^{10}$ together form an oxo group. In a second embodiment of the first aspect $R^9$ and $R^{10}$ are each hydrogen and $R^5$ is hydrogen. In a third embodiment $R^9$ and $R^{10}$ together form an oxo group, $R^5$ is hydrogen, and $R^4$ is selected from hydrogen and $C_1$-$C_3$alkylcarbonylamino. In a fourth embodiment, $R^9$ and $R^{10}$ together form an oxo group, $R^5$ is hydrogen, and $R^4$ is hydrogen.

In a fifth embodiment of the first aspect the present disclosure provides a compound of formula (I), or a pharmaceutically acceptable salt thereof, $R^9$ and $R^{10}$ together form an oxo group, $R^1$ and $R^2$ are independently selected from hydrogen and $C_1$-$C_3$alkyl, or, $R^1$ and $R^2$ together are oxo.

In a sixth embodiment of the first aspect the present disclosure provides a compound of formula (I), or a pharmaceutically acceptable salt thereof, wherein wherein $R^9$ and $R^{10}$ together form an oxo group, $R^3$ is selected from $C_1$-$C_6$alkoxy, $C_2$-$C_6$alkynyl, $C_3$-$C_6$cycloalkyl optionally substituted with cyano, $C_3$-$C_6$cycloalkylamino, piperidinyl optionally substituted with $C_1$-$C_6$alkyl, and $C_1$-$C_8$alkyl, wherein the $C_1$-$C_8$alkyl is optionally substituted with one, group selected from $C_1$-$C_3$alkoxy, $C_1$-$C_3$alkoxycarbonyl, amino, aminosulfonyl, cyano, $C_1$-$C_3$dialkylamino, hydroxy, and —$NR^xR^y$; wherein $R^x$ and $R^y$, together with the nitrogen atom to which they are attached, form a five-membered ring optionally substituted with oxo.

In a seventh embodiment of the first aspect the present disclosure provides a compound of formula (I), or a pharmaceutically acceptable salt thereof, wherein:

$R^1$ and $R^2$ are independently selected from hydrogen and $C_1$-$C_3$alkyl, or, $R^1$ and $R^2$ together are oxo;

$R^3$ is selected from $C_1$-$C_6$alkoxy, $C_2$-$C_6$alkynyl, $C_3$-$C_6$cycloalkyl optionally substituted with cyano, $C_3$-$C_6$cycloalkylamino, piperidinyl optionally substituted with $C_1$-$C_6$alkyl, and $C_1$-$C_8$alkyl, wherein the $C_1$-$C_8$alkyl is optionally substituted with one, group selected from $C_1$-$C_3$alkoxy, $C_1$-$C_3$alkoxycarbonyl, amino, aminosulfonyl, cyano, $C_1$-$C_3$dialkylamino, hydroxy, and —$NR^xR^y$; wherein $R^x$ and $R^y$, together with the nitrogen atom to which they are attached, form a five-membered ring optionally substituted with oxo;

$R^4$ is selected from hydrogen and $C_1$-$C_3$alkylcarbonylamino;

$R^5$ is hydrogen; and $R^9$ and $R^{10}$ together form an oxo group.

In a second aspect the present disclosure provides composition comprising a pharmaceutically acceptable amount of a compound of formula (I), or a pharmaceutically acceptable salt thereof, and a pharmaceutically acceptable carrier.

In a third aspect the present disclosure provides a method of inhibiting adaptor associated kinase 1 (AAK1) activity, comprising contacting AAK1 with a compound of formula (I), or a pharmaceutically acceptable salt thereof.

In a fourth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fourth aspect the disease or disorder is selected from Alzheimer's disease, bipolar disorder, pain, Parkinson's disease, and schizophrenia. In a second embodiment of the fourth aspect the pain is neuropathic pain. In a third embodiment of the fourth aspect the neuropathic pain is fibromyalgia or peripheral neuropathy.

In another aspect the present disclosure provides a compound of formula (II)

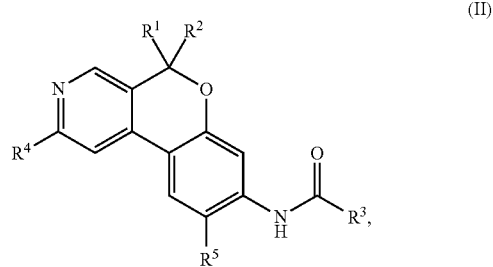

(II)

or a pharmaceutically acceptable salt thereof, wherein:

$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or $R^1$ and $R^2$ together are oxo;

$R^3$ is selected from $C_1$-$C_6$alkoxy, $C_2$-$C_6$alkynyl, amino, $C_3$-$C_6$cycloalkyl optionally substituted with $C_1$-$C_3$alkyl or cyano, $C_3$-$C_6$cycloalkylamino, piperidinyl optionally substituted with $C_1$-$C_6$alkyl, $C_1$-$C_3$alkyl-Y, and $C_1$-$C_8$alkyl, wherein the $C_1$-$C_8$alkyl is optionally substituted with one, two, or three groups independently selected from $C_1$-$C_3$alkoxy, $C_1$-$C_3$alkylamino, $C_1$-$C_3$alkoxy$C_2$-$C_3$alkylamino, $C_1$-$C_3$alkoxycarbonyl, amino, aminosulfonyl, aryl, cyano, $C_1$-$C_3$dialkylamino, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, and hydroxy;

$R^5$ is selected from hydrogen, $C_1$-$C_3$alkyl, cyano, $C_3$cycloalkyl, and halo;

$R^x$ and $R^y$, together with the nitrogen atom to which they are attached, form a three- to six-member ring optionally substituted with oxo; and Y is selected from

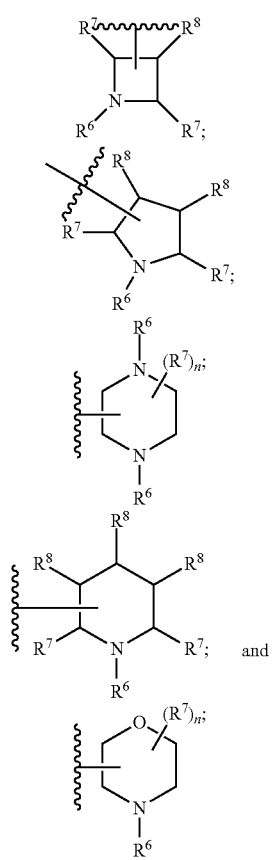

wherein $R^6$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^7$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^8$ is independently selected from hydrogen, $C_1$-$C_3$alkoxy and hydroxy.

Other aspects of the present disclosure may include suitable combinations of embodiments disclosed herein.

Yet other aspects and embodiments may be found in the description provided herein.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^6$ groups may be the same or different.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylamino," as used herein, refers to —NHR wherein R is an alkoxyalkyl group.

The term "alkoxycarbonyl," as used herein, refers to an alkoxy group attached to the parent molecular moiety through a carbonyl group.

The term "alkoxycarbonylamino," as used herein, refers to an —NHR wherein R is an alkoxycarbonyl group.

The term "alkyl," as used herein, refers to a group derived from a straight or branched chain saturated hydrocarbon.

The term "alkylamino," as used herein refers to —NHR, wherein R is an alkyl group.

The term "alkylcarbonyl," as used herein, refers to an alkyl group attached to the parent molecular moiety through a carbonyl group.

The term "alkylcarbonylamino," as used herein, refers to —NHR wherein R is an alkylcarbonyl group.

The term "alkynyl," as used herein, as used herein, refers to a straight or branched chain group containing at least one carbon-carbon triple bond.

The term "amino," as used herein, refers to —$NH_2$.

The term "aminosulfonyl," as used herein, refers to —$SO_2NH_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl.

The term "arylalkyl," as used herein, refers to an alkyl group substituted with one, two, or three aryl groups.

The term "arylamino," as used herein, refers to —NHR wherein R is an aryl group.

The term "arylcarbonyl," as used herein, refers to an aryl group attached to the parent molecular moiety through a carbonyl group.

The term "arylcarbonylamino," as used herein refers to —NHR wherein R is an arylcarbonyl group.

The term "carbonyl," as used herein, refers to —C(O)—.

The term "cyano," as used herein, refers to —CN.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "cycloalkylamino," as used herein, refers to —NHR wherein R is a cycloalkyl group.

The term "cycloalkylcarbonyl," as used herein, refers to a cycloalkyl group attached to the parent molecular moiety through a carbonyl group.

The term "cycloalkylcarbonylamino," as used herein, refers to —NHR wherein R is a cycloalkylcarbonyl group.

The term "cycloalkyloxy," as used herein, refers to a cycloalkyl group attached to the parent molecular moiety through an oxygen atom.

The term "dialkylamino," as used herein, refers to NR$_2$, wherein each R is an alkyl group. The two alkyl groups are the same or different.

The term "halo," as used herein, refers to Br, Cl, F, and/or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylamino," as used herein, refers to —NHR wherein R is a haloalkyl group.

The term "haloalkylcarbonyl," as used herein, refers to a haloalkyl group attached to the parent molecular moiety through a carbonyl group.

The term "haloalkylcarbonylamino," as used herein, refers to —NHR wherein R is a haloalkylcarbonyl group.

The term "hydroxy," as used herein, refers to —OH.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipetidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as *acacia*, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers.

Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC for 1-(3-dimethylaminopropyl)-3-ethylcarbodiimide hydrochloride; TBTU for O-benzotriazol-1-yl-N,N,N',N'-tetramethyluronium tetrafluoroborate; THF for tetrahydrofuran; DMF for N,N-dimethylformamide; RT or rt or r.t. for room temperature or retention time (context will dictate); $t_R$ for retention time; DCM for dichloromethane; dppf for 1,1'-bis(diphenylphosphanyl) ferrocene; LDA for lithium diisopropylamide; Ph for phenyl; BOC or Boc for tert-butoxycarbonyl; OAC or OAc for acetate; Ac for acetyl; AcCN, ACN, or MeCN for acetonitrile; MeOH for methanol; EtOH for ethanol; EtOAc or EtOAC for ethyl acetate; h for hours; min for minutes; TFA for trifluoracetic acid; BHT for 3,5-di-tert-butyl-4-hydroxytoluene; DBU for 1,8-diazabicycloundec-7-ene; DIEA or DIPEA for diisopropylethylamine; DMSO for dimethylsulfoxide; DCE for 1,2-dichloroethane; and MeOD for $CD_3OD$.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 8, wherein $R^1$ and $R^2$ are H, alkyl, cycloalkyl or alkenyl, are prepared by the methods outlined in Scheme 1. The appropriate phenolate can be alkylated with a suitably substituted propargyl halide at ambient temperature to provide the desired propargyl ether 2. Wittig reaction of the aldehyde function in 2 with appropriate Wittig reagent can result in the formation of the desired olefin as mixture of E, Z mixture with the E-isomer being the major product. The α,β-unsaturated aldehyde isomeric mixture 3 thus obtained can be converted to hydrazone derivative 4 by reaction with 1,1-dimethylhydrazine in a solvent such as dichloromethane in presence of a dehydrating agent such as $MgSO_4$. The crude hydrazone 4 thus obtained can be subjected to an intramolecular [4+2] cycloaddition reaction in presence of a radical scavenger such as 2,6-di-tert-butyl-4-methylphenol in a solvent such as mesitylene (Dolle, R. E. et. al. *Tetrahedron Lett.* 1988, 29, 6349-6352) to provide the cyclization product 5. The bromide in 5 can be replaced by reaction with a protected amine in a palladium catalyzed coupling reaction using reaction conditions familiar to those skilled in the art. The protecting group can subsequently be unmasked by the methods as described in *Protective Groups in Organic Synthesis* (Greene, Wuts; $3^{rd}$ ed., 1999, John Wiley & Sons, Inc.) to give intermediates 7. Compounds of formula 7, can be coupled with a carboxylic acid ($R^3C(O)OH$) using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 8. Alternatively, compounds of formula 7 can be coupled with an acid chloride ($R^3C(O)Cl$). If $R^3$ contains an amine group or another functional group that is protected, the protecting group can be removed by treating the substrate with the appropriate reagents as described in *Protective Groups in Organic Synthesis* (Greene, Wuts; $3^{rd}$ ed., 1999, John Wiley & Sons, Inc.) to provide compounds of formula (I) wherein $R^1$ and $R^2$=H, alkyl, cycloalkyl or alkenyl.

Scheme 1

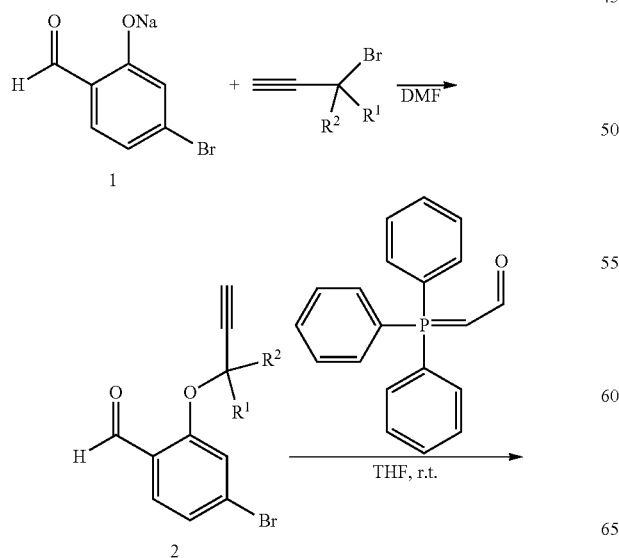

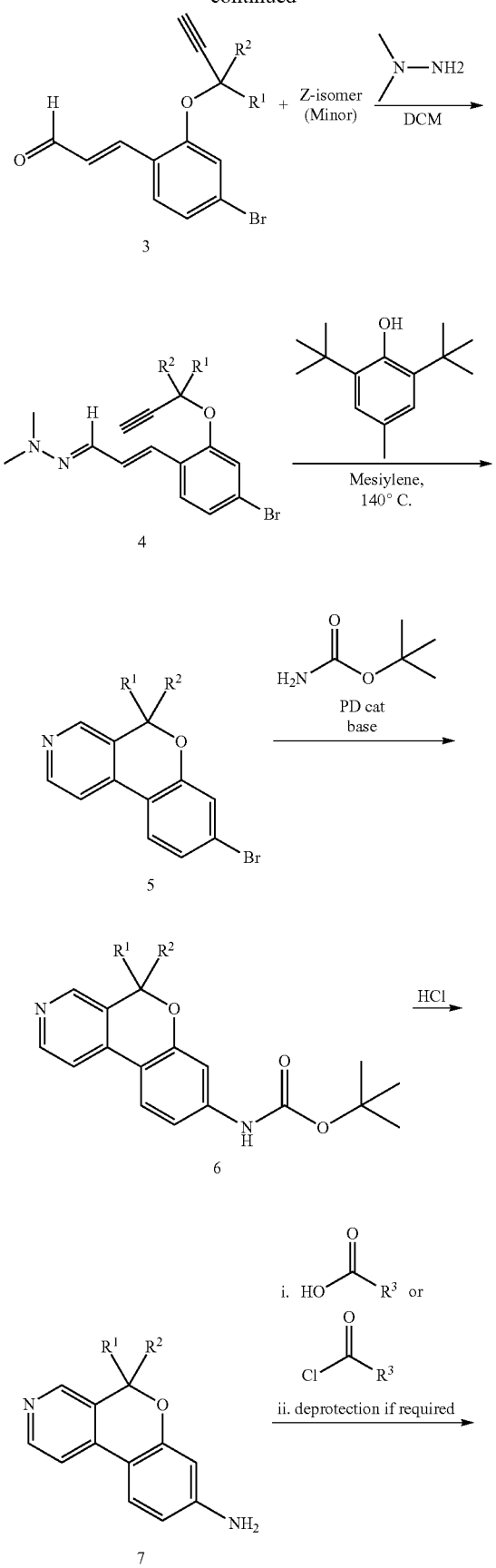

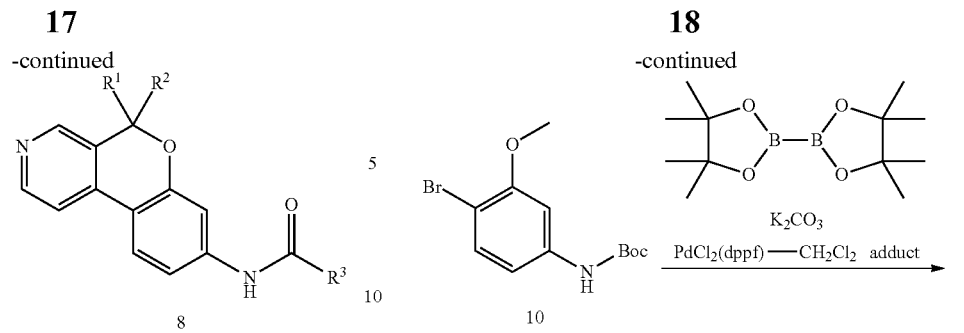

Compounds of formula 17 or 18, wherein $R^1$ and $R^2$ are H can be prepared by the methods outlined in Scheme 2. Aniline 9 can be protected by treating the substrate with the appropriate reagents such as (Boc)2O as described in *Protective Groups in Organic Synthesis* (Greene, Wuts; 3rd ed., 1999, John Wiley & Sons, Inc.) to afford 10. Conversion of the bromide in 10 to a boronic ester 11 can be achieved with bis(pinacolato)diboron in the presence of a palladium catalyst such as $PdCl_2(dppf)$ and a base such as potassium acetate or potassium phosphate in a solvent such as dioxane, THF, or toluene at temperatures ranging from 20° C. to 150° C. Conversion of 12 can be affected with DMF and a base such as LDA to provide aldehyde 13. Subsequent coupling of 12 with boronate 11 under standard Suzuki coupling conditions employing a base such as cesium carbonate and a catalyst such as $Pd(PPh_3)_4$ as described by Zhang, Lei et. al. (Journal of Medicinal Chemistry, 2011, 54, 1724-1739) can provide 14. Reduction of aldehyde 14 to alcohol 15 can occur using a reducing reagent such as sodium borohydride. Alcohols 15, upon treatment with a hydride source such as sodium hydride in a solvent such as THF under inert atmosphere at 100° C. can afford the deprotected, constrained core 16. Compound 16 can be coupled with a carboxylic acid ($R^3C(O)OH$) using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 17. Alternatively, compounds of formula 16 can be coupled with an acid chloride ($R^3C(O)Cl$) to afford compounds of the formula 17 or a chloroformate ($R^3OC(O)Cl$) to afford compounds of the formula 18. If $R^3$ contains an amine group or another functional group that is protected, the protecting group can be removed by treating the substrate with the appropriate reagents as described in *Protective Groups in Organic Synthesis* (Greene, Wuts; 3rd ed., 1999, John Wiley & Sons, Inc.) to provide compounds of formula (I) wherein $R^1$ and $R^2$=H.

Scheme 2

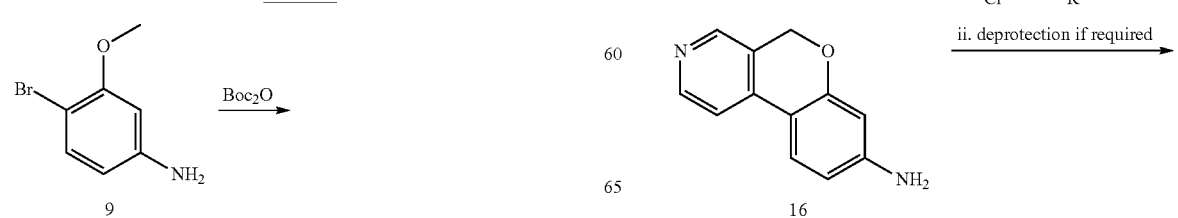

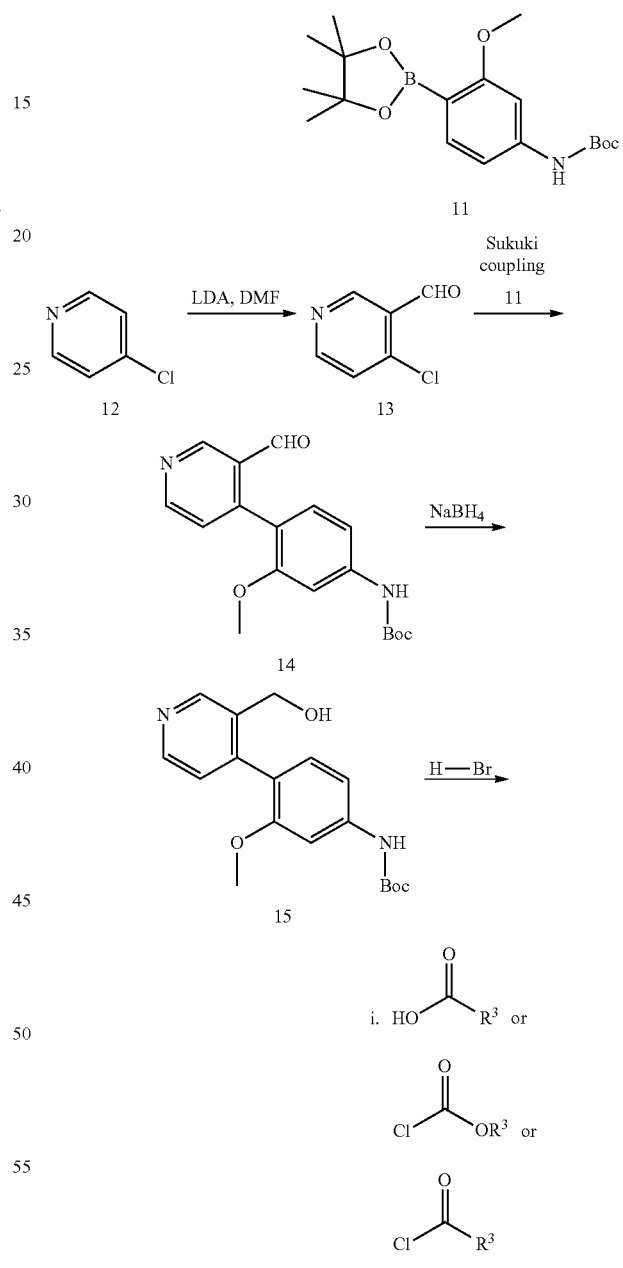

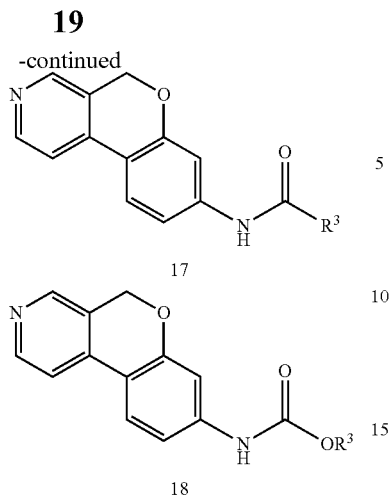

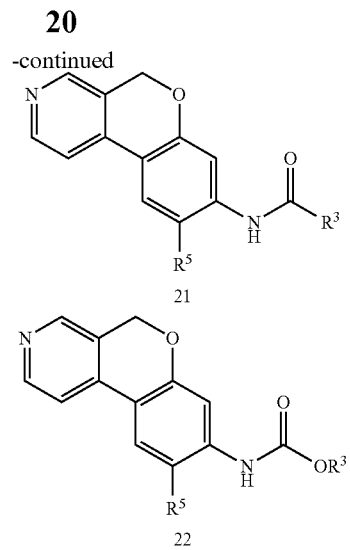

Compounds of formula 19 or 20 wherein R⁵ is halo can be prepared by the methods as outlined in Scheme 3. Compounds of formula 19 or 20 can be prepared by treatment with a halogenating agent such as N-bromosuccinamide. The halogen can be further converted to 21 or 22 via palladium catalyzed coupling reactions, including reaction conditions familiar to those skilled in the art such as a Suzuki reaction, Stille reaction, or Negishi reaction to provide compounds of formula (I) wherein R⁵=CN, alkyl, haloalkyl, aryl or heteroaryl.

Scheme 3

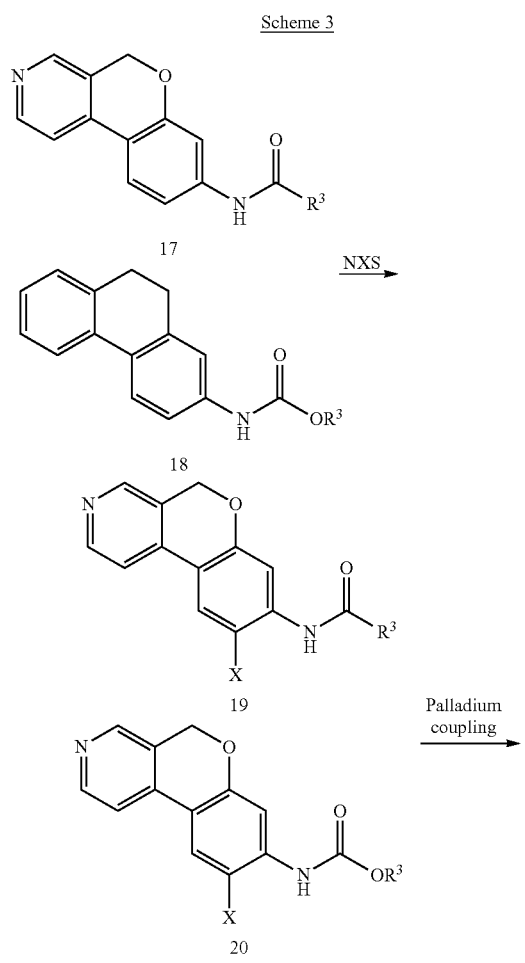

Compounds of formula 32, wherein R⁴=NHAc can be prepared by the methods outlined in Scheme 4. Conversion of the 2-fluoro-1-iodo-4-nitrobenzene to boronic ester 23 can be achieved with bis(pinacolato)diboron in the presence of a palladium catalyst such as PdCl₂(dppf) and a base such as potassium acetate or potassium phosphate in a solvent such as dioxane, THF, or toluene at temperatures ranging from 20° C. to 150° C. Halogenation of 4-chloropyridin-2-amine with a in halogenating agent such as N-bromosuccinamide can afford compound 24. Acylation of the amino group with a reagent such as acetylchloride followed by Suzuki coupling using standard conditions such as 2,4,6-trivinylcyclotriboroxane in the presence of a palladium catalyst such as Pd(PPh₃)₄ or Pd(OAc)₂ and a base such as sodium carbonate, cesium carbonate, potassium carbonate, or potassium phosphate in a solvent such as DME, DMF, toluene at elevated temperatures can furnish compounds of formula 26. Oxidative cleavage of the vinyl group using reagents such as osmium tetroxide and sodium periodate can afford aldehyde 27. Suzuki coupling of 27 and 23 using conditions employing a base such as cesium carbonate and a catalyst such as Pd(PPh3)4 as described by Zhang, Lei et. al. (Journal of Medicinal Chemistry, 2011, 54, 1724-1739) can provide 28. Reduction of aldehyde 28 to alcohol 29 can occur using a reducing reagent such as sodium borohydride. Alcohol 29, upon treatment with a hydride source such as sodium hydride in a solvent such as THF under inert atmosphere at 100° C. can afford the cyclized core 30. Compound 30 can be reduced to the amine using standard conditions such as hydrogenation with palladium on carbon to afford aniline 31. Compound 31 can be coupled with a carboxylic acid (R³C(O)OH) using standard peptide coupling reagents such as HATU, BOP, EDC, or TBTU in the presence of a base such as N,N-diisopropylethylamine and a solvent such as THF at temperatures ranging from 20° C. to 80° C. to form compounds of formula 32. Alternatively, compounds of formula 31 can be coupled with an acid chloride (R³C(O)Cl) to afford compounds of the formula 32. If R³ contains an amine group or another functional group that is protected, the protecting group can be removed by treating the substrate with the appropriate reagents as described in *Protective Groups in Organic Synthesis* (Greene, Wuts; 3rd ed., 1999, John Wiley & Sons, Inc.) to provide compounds of formula (I) wherein R⁴=NHAc.
Scheme 4
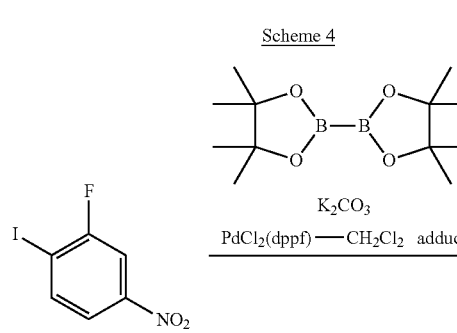
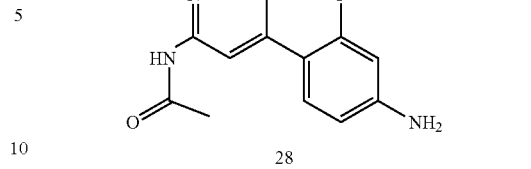
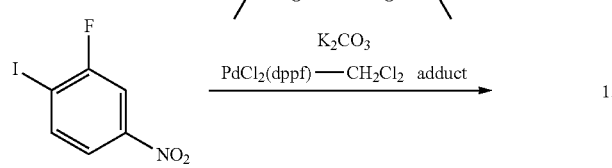
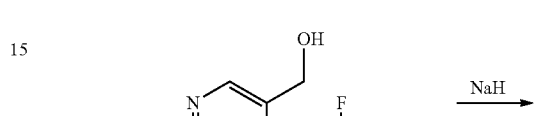
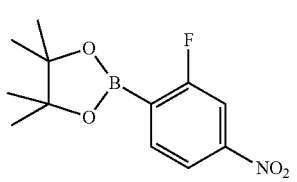
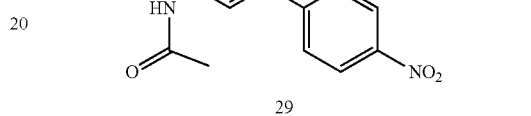
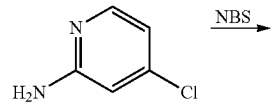
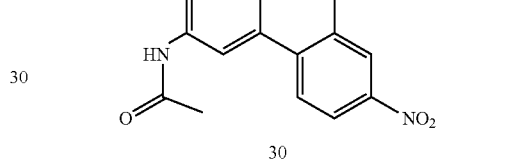
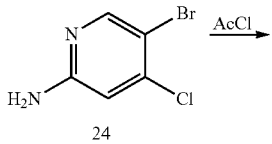
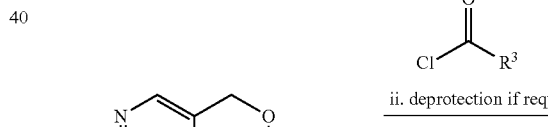
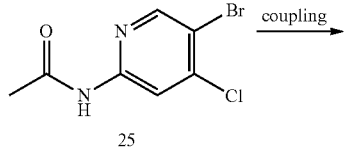
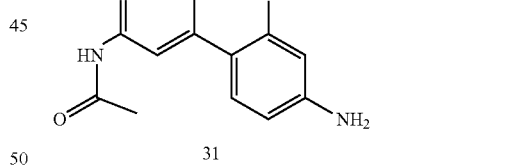
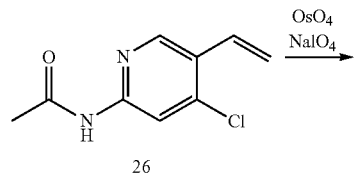
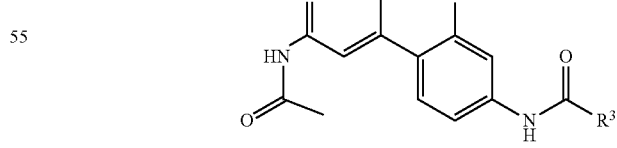
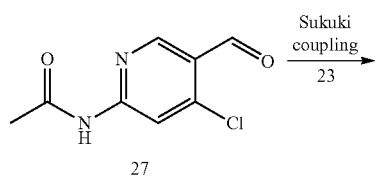
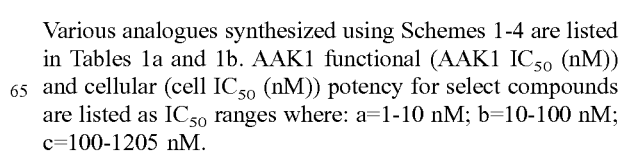
Various analogues synthesized using Schemes 1-4 are listed in Tables 1a and 1b. AAK1 functional (AAK1 IC$_{50}$ (nM)) and cellular (cell IC$_{50}$ (nM)) potency for select compounds are listed as IC$_{50}$ ranges where: a=1-10 nM; b=10-100 nM; c=100-1205 nM.

TABLE 1a (Ia)

| Ex | Stereo-chem | R¹ | R² | R⁴ | R⁵ | R³ | (M + H)⁺ | AAK1 IC$_{50}$ (nM) |
|---|---|---|---|---|---|---|---|---|
| 1 | R | H | H | H | H | (R)-CH(NH$_2$)CH$_2$CH(CH$_3$)$_2$ | 312.2 | a |
| 2 | S | H | H | H | H | (S)-CH(NH$_2$)CH$_2$CH(CH$_3$)$_2$ | 312.2 | a |
| 3 | Dia-1 | Me | H | H | H | (S)-CH(NH$_2$)CH$_2$CH(CH$_3$)$_2$ | 326.2 | 11 |
| 4 | Dia-2 | H | Me | H | H | (S)-CH(NH$_2$)CH$_2$CH(CH$_3$)$_2$ | 326.2 | 5.0 |
| 5 | Dia-mix | Me | H | H | H | (R)-CH(NH$_2$)CH$_2$CH(CH$_3$)$_2$ | 326.2 | a |
| 6 | Dia-1 | Me | H | H | H | (R)-CH(NH$_2$)CH$_2$CH(CH$_3$)$_2$ | 326.2 | a |
| 7 | Dia-2 | Me | H | H | H | (R)-CH(NH$_2$)CH$_2$CH(CH$_3$)$_2$ | 326.2 | b |
| 8 | R | Me | Me | H | H | (R)-CH(NH$_2$)CH$_2$CH(CH$_3$)$_2$ | 340.1 | b |

TABLE 1a-continued
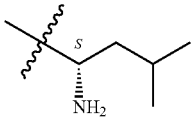
| Ex | Stereo-chem | R¹ | R² | R⁴ | R⁵ | R³ | (M + H)⁺ | AAK1 IC$_{50}$ (nM) |
|---|---|---|---|---|---|---|---|---|
| 9 | S | Me | Me | H | H | 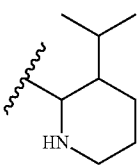 [SMILES: *C1NCCCC1C(C)C] | 340.1 | 129 |
| 10 | Dia-mix | H | H | H | H | 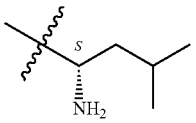 | 352.2 | 1.3 |
| 11 | S | =O | | H | H | 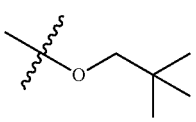 [SMILES: *OCC(C)(C)C] | 326.2 | c |
| 12 | achiral | H | H | H | H | 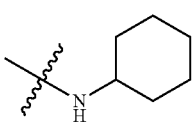 [SMILES: *NC1CCCCC1] | 313.3 | c |
| 13 | achiral | H | H | H | H | 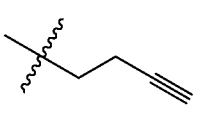 [SMILES: *CCC#C] | 324.3 | c |
| 14 | achiral | H | H | H | H | 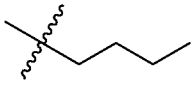 [SMILES: *CCCC] | 279.2 | b |
| 15 | achiral | H | H | H | H | 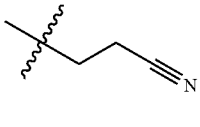 | 283.2 | 26 |
| 16 | achiral | H | H | H | H |  | 280.1 | c |
| 17 | achiral | H | H | H | H | Me | 241.2 | c |

TABLE 1a-continued (Ia)

| Ex | Stereo-chem | R$^1$ | R$^2$ | R$^4$ | R$^5$ | R$^3$ | (M + H)$^+$ | AAK1 IC$_{50}$ (nM) |
|---|---|---|---|---|---|---|---|---|
| 18 | achiral | H | H | H | H | (2-methoxyethyl, methyl) | 285.3 | c |
| 19 | achiral | H | H | H | H | (2-hydroxyethyl, methyl) | 271.2 | c |
| 20 | achiral | H | H | H | H | (1-cyanocyclopropyl) | 292.2 | c |
| 21 | achiral | H | H | H | H | (3-sulfamoylpropyl) | 348.2 | c |
| 22 | achiral | H | H | H | H | (2-(2-oxopyrrolidin-1-yl)ethyl) | 338.3 | 1203 |
| 23 | achiral | H | H | H | H | (cyclohexyl, methyl) | 309.3 | c |
| 24 | achiral | H | H | H | H | (isobutyl) | 269.2 | c |
| 25 | achiral | H | H | H | H | (cyanomethyl, methyl) | 266.2 | c |
| 26 | achiral | H | H | H | H | (neopentyl, methyl) | 297.9 | b |
| 27 | achiral | H | H | H | H | (isobutyl, methyl) | 283.2 | b |

TABLE 1a-continued
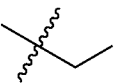
(Ia)
| Ex | Stereo-chem | R¹ | R² | R⁴ | R⁵ | R³ | (M + H)⁺ | AAK1 IC$_{50}$ (nM) |
|---|---|---|---|---|---|---|---|---|
| 28 | achiral | H | H | H | H | 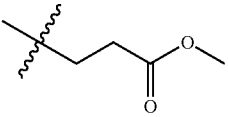 [SMILES: *CCC(=O)OC] | 255.2 | c |
| 29 | achiral | H | H | H | H | 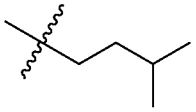 [SMILES: *CCC(C)C] | 313.2 | c |
| 30 | achiral | H | H | H | H | 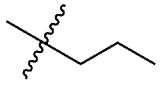 [SMILES: *CCC] | 297.3 | b |
| 31 | achiral | H | H | H | H |  | 269.2 | b |
| 32 | achiral | H | H | H | H | 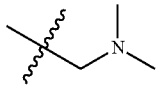 [SMILES: *CN(C)C] | 283.0 | c |
| 33 | achiral | H | H | H | H | 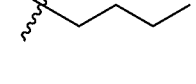 | 284.2 | c |
| 34 | achiral | H | H | H | Br | 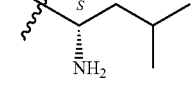 | 361.1 | b |
| 35 | S | H | H | NHAc | H | 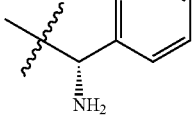 | 369.8 | b |
| 36 | S | H | H | H | H | 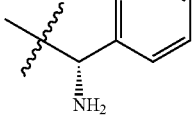 | 332.2 | 8.9 |

TABLE 1b (Ib)

| Ex | Stereo-chem | $R^1$ | $R^2$ | $R^4$ | $R^5$ | $R^3$ | $(M + H)^+$ | AAK1 $IC_{50}$ (nM) |
|----|---|---|---|---|---|---|---|---|
| 37 | S | H | H | H | H | (1-phenyl-ethylamine, R config) | 318.1 | b |

In the following examples, proton NMR spectra were recorded on either a Bruker 400 or 500 MHz NMR spectrometer. Chemical shifts are reported in δ values relative to tetramethylsilane. Liquid chromatography (LC)/mass spectra (MS) were run on a Shimadzu LC coupled to a Waters Micromass ZQ using at least one of the following methods. HPLC retention times were obtained using at least one of the following methods.

LC-MS Methods:

Method A: Phenomenex C18 2×50 mm (3 μm), A=95% H₂O/5% MeCN, B=95% MeCN/5% H₂O, Modifier 10 mM NH₄OAc, 0.00 min=0% B, 4 min=100% B 5 min=100% B, Flow rate=0.8 mL/min Method B: Phenomenex C18 2×50 mm (3 μm), A=95% H₂O/5% ACN, B=95% MeCN/5% H₂O, Modifier 10 mM NH₄OAc, 0.00 min=30% B, 4 min=100% B 5 min=100% B, Flow rate=0.8 mL/min LC/MS Method C=Column: PUROSPHER@star RP-18 (4×55 mm), 3 μm; Buffer: 20 mM NH₄OAC in water; Mphase A: Buffer+ACN (90+10); Mphase B: Buffer+MeCN (10+90); Flow: 2.5 mL/min)

LC/MS Method D=Column: ZORBAX SB C18 (46×50 mm), 5 μm; Positive mode Mphase A: 10% MeOH—90% H₂O—0.1% TFA; Mphase B: 90% MeOH—10% H₂O—0.1% TFA; Flow: 5 mL/min)

Method E: Xbridge BEH C18 2×50 mm (2.5 μm), A=0.1% HCOOH in H₂O, B=0.07% HCOOH in MeCN, 0.00 min=10% B, 1.5 min=100% B 3 min=100% B, Flow rate=1.0 mL/min Method F: Acentis Express C18 2×50 mm (2.7 μm), Buffer: 10 mM NH₄OAC in water pH=4.5; Mphase A: Buffer+ACN (98:2); Mphase B: Buffer+MeCN (2:98); Flow: 1.0 mL/min)

Method G: Poroshell 120 3×50 mm (2.7 μm), Buffer: 10 mM NH₄OAC in water pH=5 adjusted with formic acid; Mphase A: Buffer+ACN (90:10); Mphase B: Buffer+MeCN (10:90); Flow: 1.5 mL/min)

Chiral HPLC Methods:

Method A: CHIRALCEL OJH (250×4.6) mm 5 micron
Mob. phase: 0.2% DEA in n-hexane:ethanol (80:20)

Example 1

(R)-2-amino-N-(5H-chromeno[3,4-c]pyridin-8-yl)-4-methylpentanamide

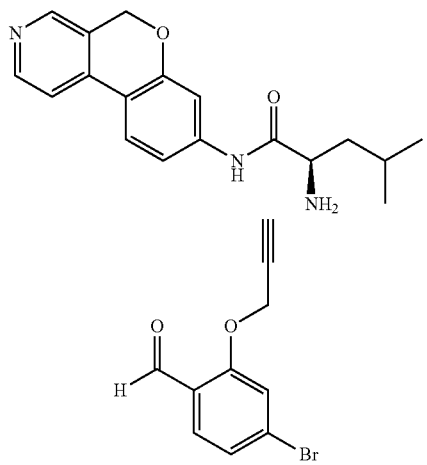

Part A. 4-bromo-2-(prop-2-ynyloxy)benzaldehyde

A solution of 4-bromo-2-hydroxybenzaldehyde (3.0 g, 24.9 mmol) in MeOH (150 mL) was treated with 1N aq. NaOH (15.7 mL, 1.05 equiv). The resulting pale yellow solution was concentrated under reduced pressure. EtOH (30 mL) was added to the residue and the solution was concentrated under reduced pressure. This was repeated with EtOH (30 mL) and then with heptane (50 mL). The resulting yellow, powdery sodium salt was dissolved in DMF (60 mL) with stirring and to it was added propargyl bromide in toluene (80 wt %, 2.33 mL, 1.4 equiv). The reaction mixture was stirred at ambient temperature for 22 h, after which time the volatiles were removed under reduced pressure. The residue was partitioned between EtOAc (70 mL) and water (40 mL). The organic layer was separated and treated with charcoal (~1 g) then dried (Na₂SO₄) and filtered. The filtrate was concentrated under reduced pressure. The residue obtained was crystallized from EtOAc and hexane (3:7). Crop I afforded 4-bromo-2-(prop-2-ynyloxy)benzaldehyde (893 mg) as colorless needles. The mother liquor was concentrated under reduced pressure and crystallized again from EtOAc and hexane (7:93) to obtain a further Crop II of 4-bromo-2-(prop-2-ynyloxy)benzaldehyde (1.9 g). The mother liquor was concentrated again and subjected to one more crystallization as described before. Crop III yielded additional 4-bromo-2-(prop-2-ynyloxy)benzaldehyde (344 mg). All three crops were combined to give a total of 3.14 g (87% yield) of 4-bromo-2-(prop-2-ynyloxy)benzaldehyde as colorless needles. $^1$H NMR (500 MHz, CDCl₃) δ ppm 10.43 (s, 1H), 7.74 (d, J=8.2 Hz, 1H), 7.31 (d, J=1.5 Hz, 1H), 7.24-7.28 (m, 1H), 4.85 (d, J=2.4 Hz, 2H), 2.64 (t, J=2.4 Hz, 1H); LCMS (ESI) m/e 239.0, 241.0 Br pattern [(M+H)⁺, calcd for $C_{10}H_8BrO_2$ 239.0].

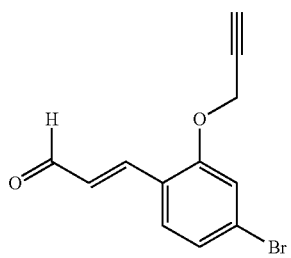

Part B. (E)-3-(4-bromo-2-(prop-2-ynyloxy)phenyl)acrylaldehyde

A mixture of 4-bromo-2-(prop-2-ynyloxy)benzaldehyde (0.852 g, 3.56 mmol) and formylmethylenetriphenylphosphorane (2.2 g, 7.12 mmol, 2 equiv) suspended in THF (20 mL) under nitrogen was stirred at ambient temperature for 18 h and then at 50° C. for another 24 h. The reaction mixture was filtered through a bed of silica gel (~25 g) eluting with EtOAc:hexane (1:4, 300 mL). The filtrate was concentrated under reduced pressure and the residue was purified by silica gel chromatography using a linear gradient of EtOAc:hexane (1:19 to 1:9). Pooled fractions containing the title compound and its Z-isomer in the ratio of (39:11, by NMR) was concentrated under reduced pressure to give (E)-3-(4-bromo-2-(prop-2-ynyloxy)phenyl)acrylaldehyde (0.69 g, 57% yield). $^1$H NMR (500 MHz, CDCl₃) δ 9.71 (d, J=7.6 Hz, 1H), 7.77 (d, J=16.2 Hz, 1H), 7.45 (d, J=8.2 Hz, 1H), 7.26-7.17 (m, 2H), 6.77 (dd, J=16.2, 7.6 Hz, 1H), 4.82 (d, J=2.4 Hz, 1H), 4.80-4.75 (m, 1H), 2.62 (t, J=2.4 Hz, 1H). The Z-isomer showed the aldehydic proton at δ 9.87 (d, J=7.9 Hz) and a smaller cis-coupling (J=11.4 Hz) for the olefinic proton at δ 6.22; LCMS (ESI) m/e 265.0, 267.0 Br pattern [(M+H)⁺, calcd for $C_{12}H_{10}BrO_2$ 265.0].

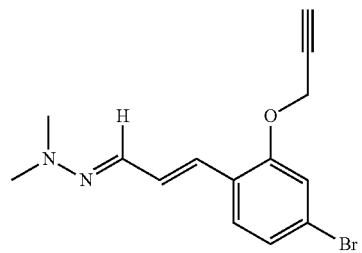 [SMILES: C#CCOc1cc(Br)ccc1/C=C/C=N/N(C)C]

Part C. (E)-2-((E)-3-(4-bromo-2-(prop-2-ynyloxy)phenyl)allylidene)-1,1-dimethylhydrazine A solution of (E)-3-(4-bromo-2-(prop-2-ynyloxy)phenyl)acrylaldehyde (2.85 g, 10.8 mmol) in dichloromethane (200 mL) containing anhydrous MgSO₄ (16 g) was cooled in an ice bath with stirring. To the ice-cold solution was added 1,1-dimethylhydrazine (2.45 mL, 32.4 mmol) dropwise and the reaction mixture was allowed to warm up to ambient temperature and was stirred for 18 h. The volatiles were concentrated under reduced pressure and the residue was coevaporated sequentially with dichloromethane (50 mL), dichloroethane (50 mL) and heptane (50 mL). (E)-2-((E)-3-(4-bromo-2-(prop-2-ynyloxy)phenyl)allylidene)-1,1-dimethylhydrazine (2.7 g, 90% yield, 90% purity) was obtained as a yellow powder. $^1$H NMR (500 MHz, CDCl₃) δ 7.39 (d, J=7.9 Hz, 1H), 7.20-7.10 (m, 3H), 7.00-6.86 (m, 2H), 4.75 (d, J=2.3 Hz, 2H), 2.95 (s, 6H), 2.58 (t, J=2.3 Hz, 1H); LCMS (ESI) m/e 307.0, 309.0 Br pattern [(M+H)⁺, calcd for $C_{14}H_{16}BrN_2O$ 307.0].

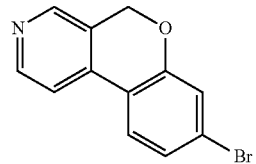 [SMILES: Brc1ccc2c(c1)OCc1cnccc1-2]

Part D. 8-bromo-5H-chromeno[3,4-c]pyridine

A solution of (E)-2-((E)-3-(4-bromo-2-(prop-2-ynyloxy)phenyl)allylidene)-1,1-dimethylhydrazine (116 mg, 374 mmol) and 2,6-di-tert-butyl-4-methylphenol (82 mg, 374 mmol) in mesitylene (4.5 mL) was degassed at 50° C. by bubbling argon for ~15 min while sonicating in a thick glass vial. The vial was capped under argon and heated to 140° C. in an oil bath with stirring for 138 h. The reaction mixture was cooled to ambient temperature and the solvent was concentrated under reduced pressure. The dark residue was purified by silica gel chromatography with EtOAc:Dichloromethane (1:19) as the eluant. Fractions containing the required product were combined and concentrated under reduced pressure to give 8-bromo-5H-chromeno[3,4-c]pyridine (27 mg, 25% yield based on 89% purity) as a pale yellow powder. $^1$H NMR (500 MHz, CDCl₃) δ 8.63 (d, J=5.2 Hz, 1H), 8.45 (s, 1H), 7.62 (d, J=8.2 Hz, 1H), 7.52 (d, J=5.2 Hz, 1H), 7.27-7.22 (m, 2H), 5.20 (s, 2H); LCMS (ESI) m/e 262.0, 264.0 Br pattern [(M+H)⁺, calcd for $C_{12}H_9BrNO$ 262.0].

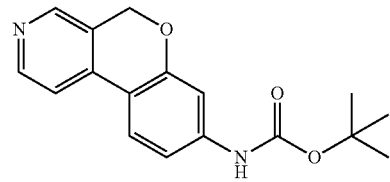 [SMILES: CC(C)(C)OC(=O)Nc1ccc2c(c1)OCc1cnccc1-2]

Part E. tert-butyl 5H-chromeno[3,4-c]pyridin-8-ylcarbamate

A solution of 8-bromo-5H-chromeno[3,4-c]pyridine (2.5 g, 9.54 mmol), tert-butyl carbamate (6.25 g, 53.3 mmol), Cs$_2$CO$_3$ (16.5 g, 50.7 mmol), XANTPHOS (1.27 g, 2.194 mmol), and palladium (II) acetate (1.33 g, 5.91 mmol), in 1,4-dioxane (20 mL) was degassed for 5 min with nitrogen. The tube was sealed and heated to 90° C. for 12 h. The mixture was filtered through diatomaceous earth (Celite®) and the filtrate concentrated under reduced pressure. Water was added and the residue extracted with ethyl acetate (3×20 mL). The combined organics were washed with brine (1×20 mL), dried over sodium sulfate, filtered and concentrated under reduced pressure. The residue was purified by preparative TLC (40% ethyl acetate in petroleum ether) to afford tert-butyl 5H-chromeno[3,4-c]pyridin-8-ylcarbamate (2.0 g, 6.70 mmol, 70% yield); LCMS (ESI) m/e 299.2 [(M+H)$^+$, calcd for C$_{17}$H$_{19}$N$_2$O$_3$ 299.1].

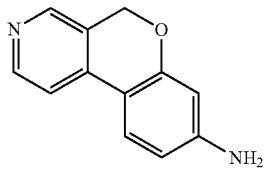

Part F. 5H-chromeno[3,4-c]pyridin-8-amine

A solution of tert-butyl 5H-chromeno[3,4-c]pyridin-8-ylcarbamate (0.157 g, 0.526 mmol) in TFA (2 mL, 26.0 mmol) was stirred at room temperature for 2 h. The TFA was removed under reduced pressure. The residue was carefully quenched with saturated sodium bicarbonate solution (10 mL) and extracted with DCM (3×10 mL). The combined organics were washed with brine (1×10 mL), dried over sodium sulfate, filtered, and concentrated under reduced pressure to afford 5H-chromeno[3,4-c]pyridin-8-amine (0.03 g, 0.151 mmol, 29% crude yield) as yellow solid which was taken into next step without further purification. LCMS (ESI) m/e 199.2 [(M+H)$^+$, calcd for C$_{12}$H$_{11}$N$_2$O 199.1].

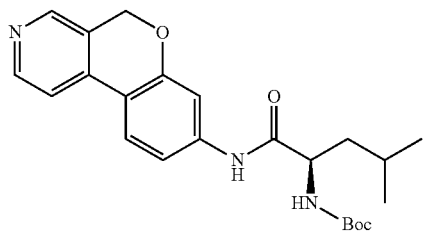 [SMILES: CC(C)C[C@@H](NC(=O)OC(C)(C)C)C(=O)Nc1ccc2c(c1)OCc1cnccc1-2]

Part G. (R)-tert-butyl (1-((5H-chromeno[3,4-c]pyridin-8-yl)amino)-4-methyl-1-oxopentan-2-yl)carbamate To a stirred solution of 5H-chromeno[3,4-c]pyridin-8-amine (0.35 g, 1.77 mmol) and (R)-2-((tert-butoxycarbonyl)amino)-4-methylpentanoic acid (0.408 g, 1.77 mmol) in pyridine (10 mL) at −10° C. was added POCl$_3$ (0.21 mL, 2.30 mmol) dropwise and the reaction mixture was stirred at this temperature for 30 min. The mixture was concentrated under reduced pressure, diluted with water (15 mL) and extracted with ethyl acetate (3×15 mL). The combined organics were washed with brine (1×10 mL), dried over sodium sulfate, filtered, and concentrated under reduced pressure. The residue was purified by preparative TLC using 50% Ethyl acetate in hexane to afford (R)-tert-butyl (1-((5H-chromeno[3,4-c]pyridin-8-yl)amino)-4-methyl-1-oxopentan-2-yl)carbamate (0.5 g, 1.22 mmol, 69% yield). LCMS (ESI) m/e 412.2 [(M+H)$^+$, calcd for C$_{23}$H$_{30}$N$_3$O$_4$ 412.2].

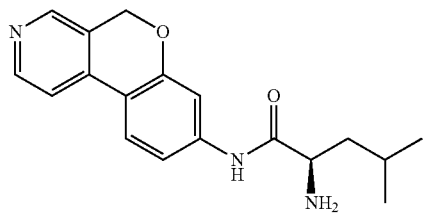 [SMILES: CC(C)C[C@@H](N)C(=O)Nc1ccc2c(c1)OCc1cnccc1-2]

Part H. (R)-2-amino-N-(5H-chromeno[3,4-c]pyridin-8-yl)-4-methylpentanamide

A solution of (R)-tert-butyl (1-((5H-chromeno[3,4-c]pyridin-8-yl)amino)-4-methyl-1-oxopentan-2-yl)carbamate (300 mg, 0.729 mmol) in TFA (562 μl, 7.29 mmol) was stirred at room temperature for 10 h. The solvent was concentrated under reduced pressure and the residue purified by preparative HPLC to give (R)-2-amino-N-(5H-chromeno[3,4-c]pyridin-8-yl)-4-methylpentanamide (28 mg, 0.09 mmol, 12% yield) as a yellow solid. $^1$H NMR (500 MHz, METHANOL-d$_4$) δ 8.66 (d, J=6.1 Hz, 1H), 8.62 (s, 1H), 8.18 (d, J=6.1 Hz, 1H), 8.05 (d, J=8.9 Hz, 1H), 7.59 (d, J=2.1 Hz, 1H), 7.41 (dd, J=8.5, 2.1 Hz, 1H), 5.35 (s, 2H), 4.07 (t, J=7.2 Hz, 1H), 1.88-1.71 (m, 3H), 1.06 (d, J=0.9 Hz, 3H), 1.05 (d, J=0.9 Hz, 3H); LCMS (ESI) m/e 312.2 [(M+H)$^+$, calcd for C$_{18}$H$_{22}$N$_3$O$_2$ 312.2].

Example 2

(S)-2-amino-N-(5H-chromeno[3,4-c]pyridin-8-yl)-4-methylpentanamide

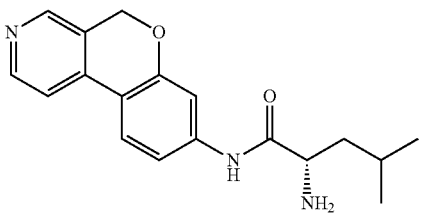 [SMILES: CC(C)C[C@H](N)C(=O)Nc1ccc2c(c1)OCc1cnccc1-2]

The title compound was prepared following the same protocol described in Example 1 using (S)-2-((tert-butoxycarbonyl)amino)-4-methylpentanoic acid in Part G to give (S)-2-amino-N-(5H-chromeno[3,4-c]pyridin-8-yl)-4-methylpentanamide. $^1$H NMR (500 MHz, METHANOL-d$_4$) δ 8.69 (d, J=6.1 Hz, 1H), 8.65 (s, 1H), 8.24 (d, J=6.4 Hz, 1H), 8.07 (d, J=8.9 Hz, 1H), 7.62 (d, J=2.1 Hz, 1H), 7.43 (dd, J=8.7, 2.0 Hz, 1H), 5.37 (s, 2H), 4.09 (t, J=7.2 Hz, 1H), 1.88-1.73 (m, 3H), 1.08-1.06 (m, 1H), 1.06-1.05 (m, 1H), 1.07 (s, 3H), 1.06 (s, 3H); LCMS (ESI) m/e 312.2 [(M+H)$^+$, calcd for $C_{18}H_{22}N_3O_2$ 312.2].

Example 3 and 4

(S)-2-amino-4-methyl-N—((R)-5-methyl-5H-chromeno[3,4-c]pyridin-8-yl)pentanamide and (S)-2-amino-4-methyl-N—((S)-5-methyl-5H-chromeno[3,4-c]pyridin-8-yl)pentanamide

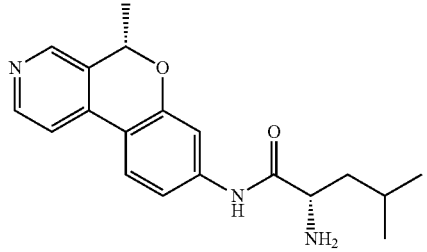

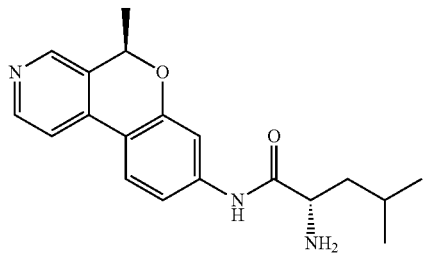

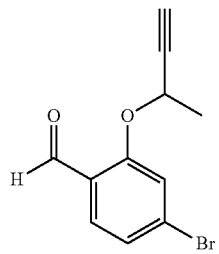

Part A. 4-bromo-2-(but-3-yn-2-yloxy)benzaldehyde

To a solution of 4-bromo-2-hydroxybenzaldehyde (3.0 g, 14.92 mmol) in DMF (60 mL) was added $K_2CO_3$ (2.063 g, 14.92 mmol). The reaction mixture was cooled to 0° C. and 3-bromobut-1-yne (2.98 g, 22.39 mmol) was added dropwise over a period of 10 min. The mixture was allowed to warm to RT and stirred for 16 h. The reaction solution was poured into 200 mL of ice cold water. The solid obtained was collected by vacuum filtration and air dried. Obtained 4-bromo-2-(but-3-yn-2-yloxy)benzaldehyde (3.0 g, 11.02 mmol, 74% yield) as a brown oil. $^1$H NMR (400 MHz, CDCl$_3$) δ 10.41 (s, 1H), 7.71 (d, J=8.4 Hz, 1H), 7.36 (d, J=1.6 Hz, 1H), 7.22 (d, J=8.4 Hz, 1H), 4.95 (dq, J=2.0 Hz, J=2.0 Hz, 1H), 2.62 (d, J=2.0 Hz, 1H); 1.74 (d, J=2.0 Hz, 3H); LCMS (ESI) m/e 253.0, 255.0 Br pattern [(M+H)$^+$, calcd for $C_{11}H_{10}BrO_2$ 253.0].

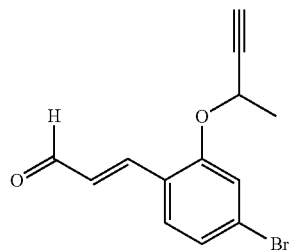 [SMILES: C#CC(C)Oc1cc(Br)ccc1/C=C/C=O]

Part B. 3-(4-bromo-2-(but-3-yn-2-yloxy)phenyl)acrylaldehyde

To a solution of 4-bromo-2-(but-3-yn-2-yloxy)benzaldehyde (3.0 g, 11.85 mmol) in tetrahydrofuran (60 mL) was added 2-(triphenylphosphoranylidene)acetaldehyde (4.69 g, 15.40 mmol). The reaction mixture was heated at 50° C. for 90 h. The reaction mixture was cooled to room temperature and quenched with brine (100 mL). The solution was extracted with ethyl acetate (3×100 mL). The combined organics were dried over Na$_2$SO$_4$, filtered, and concentrated under reduced pressure. The crude product was purified by via silica gel chromatography (pet ether:ethyl acetate) to afford 3-(4-bromo-2-(but-3-yn-2-yloxy)phenyl)acrylaldehyde (1.3 g, 4.19 mmol, 35% yield) as a yellow solid. LCMS (ESI) m/e 279.0, 281.0 Br pattern [(M+H)+, calcd for $C_{13}H_{12}BrO_2$ 279.0].

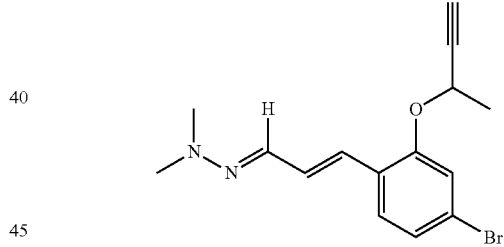

Part C. 2-(3-(4-bromo-2-(but-3-yn-2-yloxy)phenyl)allylidene)-1,1-dimethylhydrazine To a solution of 3-(4-bromo-2-(but-3-yn-2-yloxy)phenyl)acrylaldehyde (1.3 g, 4.66 mmol) in (52 mL) was added magnesium sulfate monohydrate (7.8 g, 56.4 mmol). The reaction mixture was cooled to 0° C. and 1,1-dimethylhydrazine (1.08 mL, 13.97 mmol) was added dropwise over a period of 5 min. The reaction mixture was then allowed warm to room temperature and stirred for 16 h. The reaction mixture was filtered through a bed of magnesium sulfate, washed with dichloromethane (100 mL), and concentrated under reduced pressure to obtain 2-(3-(4-bromo-2-(but-3-yn-2-yloxy)phenyl)allylidene)-1,1-dimethylhydrazine (1.6 g, 4.63 mmol, 99% crude yield). The material was carried on without further purification. LCMS (ESI) m/e 321.0, 323.0 Br pattern [(M+H)+, calcd for $C_{15}H_{18}BrN_2O$ 321.1].

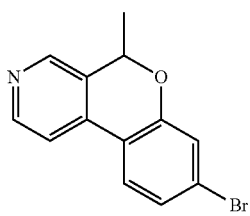 [SMILES: CC1Oc2cc(Br)ccc2-c2ccncc21]

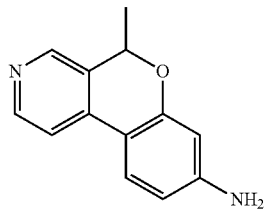

Part D.
8-bromo-5-methyl-5H-chromeno[3,4-c]pyridine

To a solution of 3-(4-bromo-2-(but-3-yn-2-yloxy)phenyl) allylidene)-1,1-dimethylhydrazine (1.9 g, 5.92 mmol) in mesitylene (120 mL, 9.72 mmol) was added BHT (0.026 g, 0.118 mmol). The solution was degassed by sonication under nitrogen for 15 min then heated at 140° C. for 96 h. The solution was cooled to room temperature and the mesitylene was removed under reduced pressure. The crude product thus obtained was purified by silica gel chromatography using a linear gradient of 5-30% of ethyl acetate in hexane to afford 8-bromo-5-methyl-5H-chromeno[3,4-c] pyridine (1.1 g, 3.98 mmol, 67% yield for two steps) as a brown oil. LCMS (ESI) m/e 276.0, 278.0 Br pattern [(M+H)+, calcd for $C_{13}H_{11}BrNO$ 276.0].

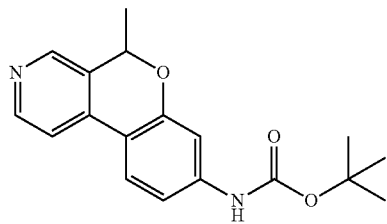 [SMILES: CC1Oc2cc(NC(=O)OC(C)(C)C)ccc2-c2ccncc21]

Part E. tert-butyl
(5-methyl-5H-chromeno[3,4-c]pyridin-8-yl)carbamate

To a 15 mL pressure tube was added 8-bromo-5-methyl-5H-chromeno[3,4-c]pyridine (275 mg, 0.996 mmol) in 1,4-dioxane (6 mL) followed by tert-butyl carbamate (652 mg, 5.57 mmol) and Cs2CO3 (1726 mg, 5.30 mmol). The reaction mixture was degassed for 10 min with nitrogen. XANTPHOS (133 mg, 0.229 mmol) and palladium(II) acetate (139 mg, 0.617 mmol) were added. The reaction mass was again degassed for 10 min. The reaction mixture was heated at 80° C. for 12 h. The mixture was cooled to room temperature, filtered through diatomaceous earth (Celite®), and washed with ethyl acetate. The filtrate was concentrated under reduced pressure. The crude product was purified via silica gel chromatography (petroleum ether: ethyl acetate) to afford tert-butyl (5-methyl-5H-chromeno [3,4-c]pyridin-8-yl)carbamate (250 mg, 0.71 mmol, 72% yield). LCMS (ESI) m/e 313.2 [(M+H)+, calcd for $C_{18}H_{21}N_2O_3$ 313.2].

Part F.
5-methyl-5H-chromeno[3,4-c]pyridin-8-amine

To a solution of tert-butyl (5-methyl-5H-chromeno[3,4-c]pyridin-8-yl)carbamate (250 mg, 0.800 mmol) in dichloromethane (5 mL) cooled to 0° C. was added 4N HCl in dioxane (5 mL, 20.00 mmol). The reaction solution was stirred at 0° C. for 5 min then at room temperature for 2 h. The solvents were removed under reduced pressure. The solid was washed with ethyl acetate to afford 5-methyl-5H-chromeno[3,4-c]pyridin-8-amine hydrochloride (185 mg, 0.744 mmol, 93% yield). LCMS (ESI) m/e 213.0 [(M+H)+, calcd for $C_{13}H_{13}N_2O$ 213.1].

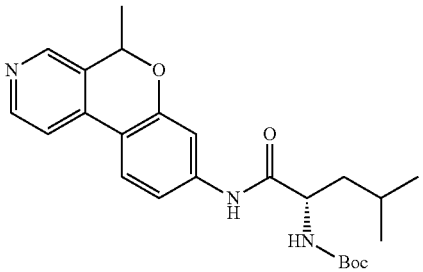 [SMILES: CC(C)C[C@H](NC(=O)OC(C)(C)C)C(=O)Nc1ccc2c(c1)OC(C)c1cnccc1-2]

Part G. tert-butyl ((2S)-4-methyl-1-((5-methyl-5H-chromeno[3,4-c]pyridin-8-yl)amino)-1-oxopentan-2-yl)carbamate To a solution of 5-methyl-5H-chromeno[3,4-c]pyridin-8-amine hydrochloride (250 mg, 1.178 mmol) in pyridine (4 mL) was added ((S)-2-((tert-butoxycarbonyl)amino)-4-methylpentanoic acid (327 mg, 1.413 mmol). The reaction mixture was cooled to −15° C. and POCl3 (0.165 mL, 1.767 mmol) was added dropwise. The reaction mixture was stirred at −15° C. for 30 min then at room temperature for 1 h. The pyridine was removed under reduced pressure. To the residue was added 25 mL of water and the solution extracted with ethyl acetate (×25 mL). The combined the organic layers were washed with 1.5N HCl (1×25 mL). The organics were dried over Na2SO4, filtered and concentrated under reduced pressure. The crude material was purified by preparative TLC (80% ethyl acetate in hexane) to afford tert-butyl ((2S)-4-methyl-1-((5-methyl-5H-chromeno[3,4-c] pyridin-8-yl)amino)-1-oxopentan-2-yl)carbamate (80 mg, 0.19 mmol, 16% yield). $^1$H NMR (500 MHz, METHANOL-$d_4$) δ 8.49 (d, J=4.8 Hz, 1H), 8.40 (s, 1H), 7.85 (d, J=8.4 Hz, 1H), 7.74 (d, J=5.2 Hz, 1H), 7.43 (dd, J=2.0 Hz, 2.0 Hz, 1H), 7.31 (d, J=8.4 Hz, 1H), 5.41 (d, J=6.8 Hz, 1H), 4.24 (s, 1H), 1.77-1.68 (m, 1H), 1.64-1.47 (m, 5H), 1.47 (s, 9H), 1.11 (d, J=3.2 Hz, 3H). 0.99 (d, J=3.2 Hz, 3H); LCMS (ESI) m/e 426.2 [(M+H)+, calcd for $C_{24}H_{32}N_3O_4$ 426.2].

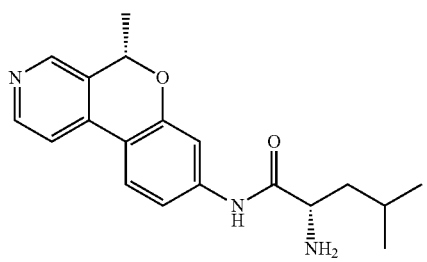 [SMILES: CC(C)C[C@@H](N)C(=O)Nc1ccc2c(c1)OC(C)c1cnccc1-2]

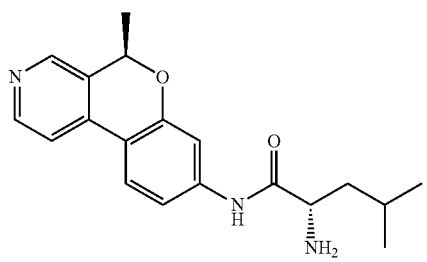

Part H. (S)-2-amino-4-methyl-N—((R)-5-methyl-5H-chromeno[3,4-c]pyridin-8-yl)pentanamide and (S)-2-amino-4-methyl-N—((S)-5-methyl-5H-chromeno[3,4-c]pyridin-8-yl)pentanamide To a solution of tert-butyl ((2S)-4-methyl-1-((5-methyl-5H-chromeno[3,4-c]pyridin-8-yl)amino)-1-oxopentan-2-yl)carbamate (80 mg, 0.188 mmol) in dichloromethane (2 mL) cooled to 0° C. was added 4N HCl in dioxane (2 mL, 8.00 mmol) slowly over a period of 2 min. The reaction mixture was stirred at 0° C. for 5 min, then warmed to room temperature and allowed to stir for 2 h. The solvents were removed under reduced pressure. The crude product was recrystallized from methanol/ethyl acetate to afford a mixture of diastereomers. The mixture was separated via chiral preparative HPLC (Method A) to afford diastereomer 1 (15 mg, 0.04 mmol, 21% yield) and diastereomer 2 (13 mg, 0.03 mmol, 21% yield). The absolute stereochemistry on the methyl was not determined: Diastereomer 1 (first eluting diastereomer): $^1$H NMR (400 MHz, METHANOL-$d_4$) δ 8.49 (d, J=5.2 Hz, 1H), 8.38 (s, 1H), 7.85 (d, J=8.4 Hz, 1H), 7.72 (d, J=5.2 Hz, 1H), 7.46 (d, J=2.0 Hz, 1H), 7.30 (dd, J=8.4 Hz, J=2.0 Hz, 1H), 5.41 (q, J=6.8 Hz, 1H), 3.59-3.55 (m, 1H), 1.81-1.77 (m, 1H), 1.70-1.66 (m, 5H), 1.02 (d, J=4.4 Hz, 3H). 1.0 (d, J=4.4 Hz, 3H); LCMS (ESI) m/e 326.2 [(M+H)+, calcd for $C_{19}H_{24}N_3O_2$ 326.2]; Diastereomer 2 (second eluting diastereomer): $^1$H NMR (400 MHz, METHANOL-$d_4$) δ 8.49 (d, J=5.2 Hz, 1H), 8.39 (s, 1H), 7.86 (d, J=8.4 Hz, 1H), 7.72 (d, J=5.2 Hz, 1H), 7.46 (d, J=2.0 Hz, 1H), 7.30 (dd, J=8.4 Hz, J=2.0 Hz, 1H), 5.41 (q, J=6.8 Hz, 1H), 3.59-3.55 (m, 1H), 1.81-1.77 (m, 1H), 1.70-1.66 (m, 5H), 1.02 (d, J=4.4 Hz, 3H). 1.0 (d, J=4.4 Hz, 3H); LCMS (ESI) m/e 326.2 [(M+H)+, calcd for $C_{19}H_{24}N_3O_2$ 326.2].

Example 5

(2R)-2-amino-4-methyl-N-(5-methyl-5H-chromeno[3,4-c]pyridin-8-yl)pentanamide

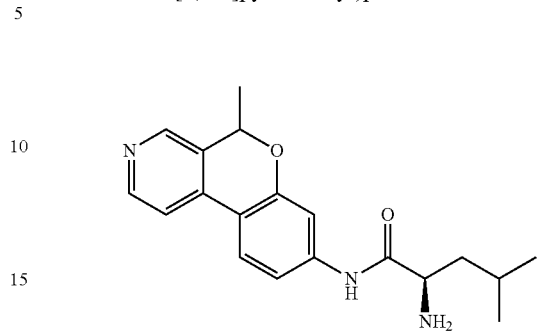

The title compound was prepared following the same protocol described in Example 3 and 4 using (R)-2-((tert-butoxycarbonyl)amino)-4-methylpentanoic acid in Part G to give (2R)-2-amino-4-methyl-N-(5-methyl-5H-chromeno[3,4-c]pyridin-8-yl)pentanamide as a 1:1 mixture of diastereomers. $^1$H NMR (500 MHz, METHANOL-$d_4$) δ 8.69 (d, J=6.4 Hz, 1H), 8.66 (s, 1H), 8.28 (d, J=6.1 Hz, 1H), 8.05 (d, J=8.5 Hz, 1H), 7.60 (dd, J=4.4, 2.0 Hz, 1H), 7.39 (ddd, J=8.7, 5.0, 2.1 Hz, 1H), 5.60-5.50 (m, 1H), 4.11 (t, J=7.2 Hz, 1H), 1.86-1.75 (m, 3H), 1.74 (d, J=3.1 Hz, 1.5H$_{dia1\ methyl}$), 1.72 (d, J=3.4 Hz, 1.5H$_{dia2\ methyl}$), 1.05 (d, J=6.4 Hz, 6H); LCMS (ESI) m/e 326.2 [(M+H)+, calcd for $C_{19}H_{24}N_3O_2$ 326.2].

Example 6 and 7

(R)-2-amino-4-methyl-N—((R)-5-methyl-5H-chromeno[3,4-c]pyridin-8-yl)pentanamide and (R)-2-amino-4-methyl-N—((S)-5-methyl-5H-chromeno[3,4-c]pyridin-8-yl)pentanamide

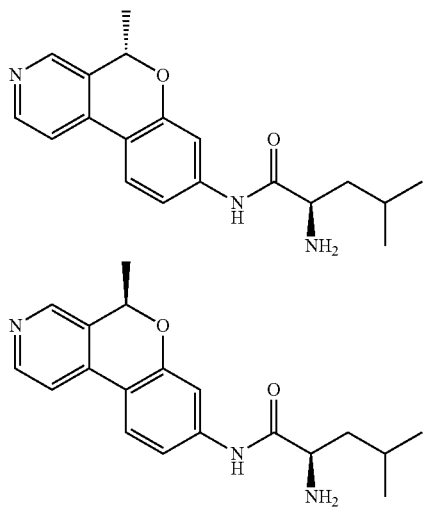

The mixture of diastereomers from Example 5 was separated by chiral HPLC (Method A) to afford diastereomer 1 (11 mg, 0.020 mmol) and diastereomer 2 (12 mg, 0.024 mmol). The absolute stereochemistry on the methyl was not determined: Diastereomer 1 (first eluting diastereomer): $^1$H NMR (500 MHz, METHANOL-d₄) δ 8.69 (d, J=6.1 Hz, 1H), 8.66 (s, 1H), 8.27 (d, J=6.1 Hz, 1H), 8.07 (d, J=8.9 Hz, 1H), 7.61 (d, J=2.1 Hz, 1H), 7.41 (dd, J=8.7, 2.0 Hz, 1H), 4.08 (t, J=7.2 Hz, 1H), 1.85-1.76 (m, 3H), 1.74 (d, J=6.7 Hz, 3H), 1.06 (d, J=1.2 Hz, 3H), 1.05 (d, J=1.2 Hz, 3H); LCMS (ESI) m/e 326.2 [(M+H)+, calcd for C$_{19}$H$_{24}$N$_3$O$_2$ 326.2]; Diastereomer 2 (second eluting diastereomer): ¹H NMR (500 MHz, METHANOL-d₄) δ 8.69 (d, J=6.1 Hz, 1H), 8.66 (s, 1H), 8.27 (d, J=6.1 Hz, 1H), 8.07 (d, J=8.9 Hz, 1H), 7.62 (d, J=2.1 Hz, 1H), 7.41 (dd, J=8.5, 2.1 Hz, 1H), 5.57 (q, J=6.6 Hz, 1H), 4.08 (t, J=7.2 Hz, 1H), 1.86-1.77 (m, 3H), 1.74 (d, J=6.7 Hz, 3H), 1.06 (d, J=0.9 Hz, 3H), 1.05 (d, J=0.9 Hz, 3H); LCMS (ESI) m/e 326.2 [(M+H)+, calcd for C$_{19}$H$_{24}$N$_3$O$_2$ 326.2].

Example 8

(R)-2-amino-N-(5,5-dimethyl-5H-chromeno[3,4-c]pyridin-8-yl)-4-methylpentanamide

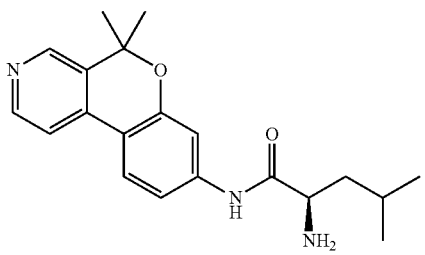 [SMILES: CC(C)C[C@@H](N)C(=O)Nc1ccc2c(c1)OC(C)(C)c1cnccc1-2]

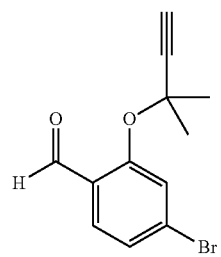

Part A. 4-bromo-2-((2-methylbut-3-yn-2-yl)oxy)benzaldehyde

To a solution of bromophenolaldehyde (2.0 g, 10.0 mmol) and cupric chloride dihydrate (43.0 mg, 0.32 mmol) in acetonitrile (33.1 mL) was added DBU (1.78 mL, 11.9 mmol) and the blue green solution was stirred in a salt-ice-water bath for 10 min. 3-Chloro-3-methyl-but-1-yne (1.13 mL, 10.0 mmol) was added from a syringe dropwise over 5 min and the reaction mixture was stirred in a salt-ice-water bath for 3.5 h. The solvent was removed under reduced pressure. The residue was taken up in EtOAc (350 mL) and washed with 1M HCl (33 mL) and water (150 mL) and brine (120 mL). The organic layer was dried (Na2SO4), filtered, and concentrated under reduced pressure. The residue was purified by silica gel chromatography (10% DCM in hexanes) to afford 4-bromo-2-((2-methylbut-3-yn-2-yl)oxy)benzaldehyde (1.82 g, 6.48 mmol, 65% yield) as a light yellow oil. ¹H NMR (500 MHz, CHLOROFORM-d) δ 10.38 (d, J=0.6 Hz, 1H), 7.83-7.62 (m, 2H), 7.33-7.29 (m, 1H), 2.71 (s, 1H), 1.77 (s, 6H) LCMS (ESI) m/e 267.0, 269.0 Br pattern [(M+H)⁺, calcd for C$_{12}$H$_{12}$BrO$_2$ 267.0].

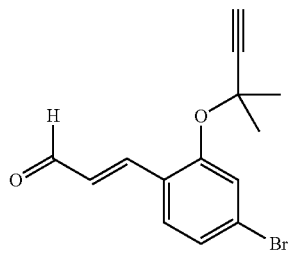 [SMILES: C#CC(C)(C)Oc1cc(Br)ccc1/C=C/C=O]

Part B. 3-(4-bromo-2-((2-methylbut-3-yn-2-yl)oxy)phenyl)acrylaldehyde

To a solution of 4-bromo-2-((2-methylbut-3-yn-2-yl)oxy)benzaldehyde (1.82 g, 6.45 mmol) in tetrahydrofuran (35 mL) was added 2-(triphenylphosphoranylidene) acetaldehyde (2.56 g, 8.4 mmol). The reaction mixture was heated at 50° C. for 90 h. The reaction mixture was cooled to room temperature and quenched with brine (100 mL). The solution was extracted with ethyl acetate (3×100 mL). The combined organics were dried over Na₂SO₄, filtered, and concentrated under reduced pressure. The crude product was purified by via silica gel chromatography (pet ether:ethyl acetate) to afford 3-(4-bromo-2-((2-methylbut-3-yn-2-yl)oxy)phenyl)acrylaldehyde (1.34 g, 3.88 mmol, 60% yield) as a yellow oil. ¹H NMR (500 MHz, CHLOROFORM-d) δ 9.71 (d, J=7.6 Hz, 1H), 7.81 (d, J=1.8 Hz, 1H), 7.76 (d, J=16.2 Hz, 1H), 7.46 (d, J=8.5 Hz, 1H), 7.24 (dd, J=8.9, 1.8 Hz, 1H), 6.73 (dd, J=16.2, 7.9 Hz, 1H), 2.71 (s, 1H), 1.77 (s, 6H); LCMS (ESI) m/e 293.0, 295.0 Br pattern [(M+H)+, calcd for C$_{13}$H$_{12}$BrO$_2$ 293.0].

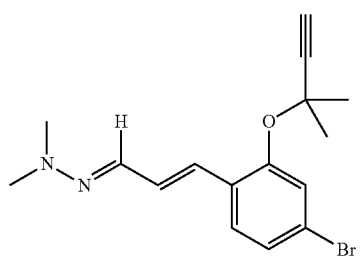 [SMILES: C#CC(C)(C)Oc1cc(Br)ccc1/C=C/C=N/N(C)C]

Part C. 2-(3-(4-bromo-2-((2-methylbut-3-yn-2-yl)oxy)phenyl)allylidene)-1,1-dimethylhydrazine To a solution of 3-(4-bromo-2-((2-methylbut-3-yn-2-yl)oxy)phenyl)acrylaldehyde (1.13 g, 3.85 mmol) in DCM (72 mL) was added magnesium sulfate monohydrate (6.5 g, 47.0 mmol). The reaction mixture was cooled to 0° C. and 1,1-Dimethylhydrazine (0.97 mL, 12.78 mmol) was added dropwise over a period of 5 min. The reaction mixture was then allowed warm to room temperature and stirred for 16 h. The reaction mixture was filtered through a bed of magnesium sulfate, washed with dichloromethane (100 mL) and concentrated under reduced pressure to obtain 2-(3-(4-bromo-2-((2-methylbut-3-yn-2-yl)oxy)phenyl)allylidene)-1,1-dimethylhydrazine (1.29 g, 3.85 mmol, 99% crude yield) as a light orange solid which was carried on without further purification. LCMS (ESI) m/e 335.1.0, 337.1 Br pattern [(M+H)+, calcd for $C_{16}H_{20}BrN_2O$ 335.1.1].

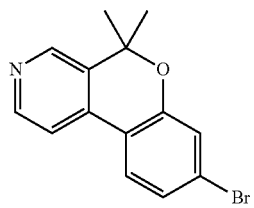

Part D.
8-bromo-5,5-dimethyl-5H-chromeno[3,4-c]pyridine

To a solution of 2-(3-(4-bromo-2-((2-methylbut-3-yn-2-yl)oxy)phenyl)allylidene)-1,1-dimethylhydrazine (1.13 g, 3.37 mmol) in mesitylene (40 mL) was added BHT (0.74 g, 3.37 mmol). The solution was degassing by sonication under nitrogen for 15 min and heated at 140° C. for 96 h. The solution was cooled to room temperature and the mesitylene was removed under reduced pressure. The crude product thus obtained was purified by silica gel chromatography (ethyl acetate/hexanes) to afford 8-bromo-5,5-dimethyl-5H-chromeno[3,4-c]pyridine (0.109 g, 0.38 mmol, 11% yield for two steps) as a brown oil. LCMS (ESI) m/e 290.0, 292.0 Br pattern [(M+H)+, calcd for $C_{14}H_{13}BrNO$ 290.0].

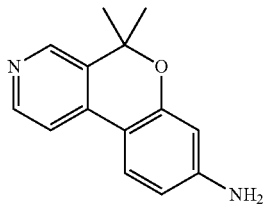

Part E.
5,5-dimethyl-5H-chromeno[3,4-c]pyridin-8-amine

To a pressure tube was added 8-bromo-5,5-dimethyl-5H-chromeno[3,4-c]pyridine (109 mg, 0.334 mmol) in 1,4-dioxane (6 mL) followed by tert-butyl carbamate (219 mg, 1.87 mmol) and $Cs_2CO_3$ (579 mg, 1.78 mmol). The reaction mixture was degassed for 10 min with nitrogen. XANTPHOS (44.5 mg, 0.077 mmol) and palladium(II) acetate (46.5 mg, 0.207 mmol) were added. The reaction mass was again degassed for 10 min. The reaction mixture was heated at 80° C. for 12 h. The mixture was cooled to room temperature, filtered through diatomaceous earth (Celite®), and washed with ethyl acetate. The filtrate was concentrated under reduced pressure. The crude product was purified via silica gel chromatography (petroleum ether:ethyl acetate) to afford 5,5-dimethyl-5H-chromeno[3,4-c]pyridin-8-amine (7.5 mg, 0.033 mmol, 10% yield) and tert-butyl (5,5-dimethyl-5H-chromeno[3,4-c]pyridin-8-yl)carbamate (35.6 mg, 0.109 mmol, 33% yield). LCMS (ESI) m/e 227.1 [(M+H)+, calcd for $C_{14}H_{15}N_2O$ 227.1] and LCMS (ESI) m/e 327.2 [(M+H)+, calcd for $C_{19}H_{23}N_2O_3$ 327.2].

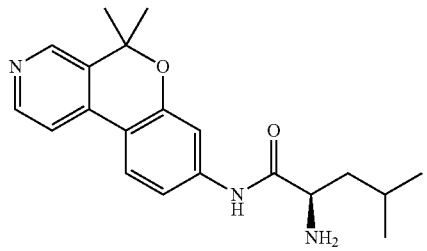

Part F. (R)-2-amino-N-(5,5-dimethyl-5H-chromeno [3,4-c]pyridin-8-yl)-4-methylpentanamide A suspension of Fmoc-D-Leucine (177 mg, 0.5 mmol) in dichloroethane (2 mL) was treated with oxalyl chloride (0.263 mL, 3 mmol) and 2 drops of DMF and stirred for 2 h. The volatiles were removed under reduced pressure. Dichloroethane (20 mL) and heptane (30 mL) were added and the mixture was concentrated under reduced pressure. Repeated two more times to remove residual oxalyl chloride. The residue was taken up in acetonitrile (0.67 mL). To a second flask was added DIEA (23 µL, 0.133 mmol) and 5,5-dimethyl-5H-chromeno[3,4-c]pyridin-8-amine (15 mg, 0.066 mmol) followed by the acid chloride solution prepared above. The reaction mixture was stirred at room temperature for 1 h. LC/MS suggested complete conversion of the starting material. The reaction mixture was concentrated under reduced pressure then reconstituted in acetonitrile (5 mL). To this was added DIEA (500 µL, 2.86 mmol) to carry out the Fmoc deprotection. The mixture was stirred at room temperature for 2 h. The solution was diluted with water (5 mL) and extracted with EtOAc (3×10 mL). The organic layers were combined and washed with brine (1×10 mL), dried (Na2SO4), filtered, and concentrated under reduced pressure. The residue was purified by silica gel chromatography (10% MeOH in DCM) to give (R)-2-amino-N-(5,5-dimethyl-5H-chromeno[3,4-c]pyridin-8-yl)-4-methylpentanamide (20.2 mg, 0.043 mmol, 65% yield). $^1H$ NMR (500 MHz, METHANOL-$d_4$) δ 8.73 (s, 1H), 8.69 (d, J=6.4 Hz, 1H), 8.32 (d, J=6.4 Hz, 1H), 8.09 (d, J=8.9 Hz, 1H), 7.60 (d, J=2.1 Hz, 1H), 7.41 (dd, J=8.7, 2.0 Hz, 1H), 4.10 (t, J=7.2 Hz, 1H), 1.87-1.81 (m, 3H), 1.79 (d, J=1.8 Hz, 6H), 1.07 (s, 3H), 1.06 (s, 3H); LCMS (ESI) m/e 340.1 [(M+H)+, calcd for $C_{20}H_{26}N_3O_2$ 340.2]; optical rotation: $[\alpha]^{20}_D$ (MeOH)=−34.71°.

Example 9

(S)-2-amino-N-(5,5-dimethyl-5H-chromeno[3,4-c] pyridin-8-yl)-4-methylpentanamide

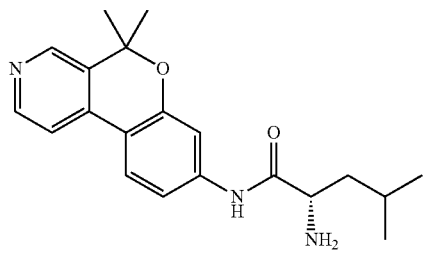 [SMILES: CC(C)C[C@H](N)C(=O)Nc1ccc2c(c1)OC(C)(C)c1cnccc1-2]

The title compound was prepared following the same protocol described in Example 8 using Fmoc-L-Leucine in Part F to give (S)-2-amino-N-(5,5-dimethyl-5H-chromeno[3,4-c]pyridin-8-yl)-4-methylpentanamide. $^1$H NMR (500 MHz, METHANOL-$d_4$) δ 8.70 (s, 1H), 8.67 (d, J=6.1 Hz, 1H), 8.25 (d, J=6.4 Hz, 1H), 8.07 (d, J=8.5 Hz, 1H), 7.58 (d, J=2.1 Hz, 1H), 7.39 (dd, J=8.9, 2.1 Hz, 1H), 4.07 (t, J=7.2 Hz, 1H), 1.87-1.79 (m, 3H), 1.78 (d, J=1.5 Hz, 6H), 1.07 (d, J=1.5 Hz, 3H), 1.06 (d, J=1.8 Hz, 3H); LCMS (ESI) m/e 340.1 [(M+H)$^+$, calcd for $C_{20}H_{26}N_3O_2$ 340.2]; optical rotation: $[\alpha]^{20}_D$ (MeOH)=+28.51°.

Example 10

N-(5H-chromeno[3,4-c]pyridin-8-yl)-3-isopropylpiperidine-2-carboxamide

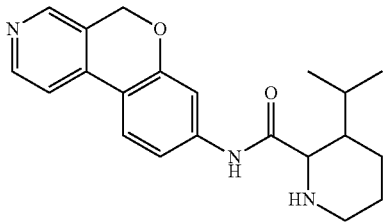 [SMILES: CC(C)C1CCCNC1C(=O)Nc1ccc2c(c1)OCc1cnccc1-2]

The title compound was prepared following the same protocol described in Example 1 using 1-(tert-butoxycarbonyl)-3-isopropylpiperidine-2-carboxylic acid in Part G to give N-(5H-chromeno[3,4-c]pyridin-8-yl)-3-isopropylpiperidine-2-carboxamide. $^1$H NMR (400 MHz, METHANOL-$d_4$) δ 8.65 (d, J=6.0 Hz, 1H), 8.60 (s, 1H), 8.12 (d, J=6.0 Hz, 1H), 8.04 (d, J=5.2 Hz, 1H), 7.56 (d, J=2.0 Hz, 1H), 7.40 (d, J=2.0 Hz, 1H), 7.37 (d, J=2.0 Hz, 1H), 5.34 (s, 2H), 3.62-3.58 (m, 1H), 3.18-3.15 (m, 1H), 2.18-2.08 (m, 2H), 1.98-1.91 (m, 2H), 1.90-1.79 (m, 2H), 1.05 (s, 3H), 1.04 (s, 3H); LCMS (ESI) m/e 352.2 [(M+H)$^+$, calcd for $C_{21}H_{26}N_3O_2$ 352.2].

Example 11

(S)-2-amino-4-methyl-N-(5-oxo-5H-chromeno[3,4-c]pyridin-8-yl)pentanamide

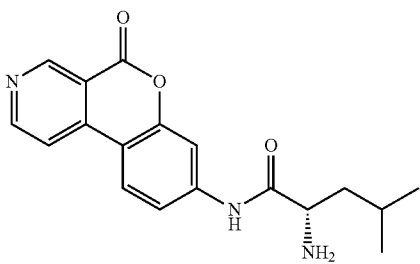 [SMILES: CC(C)C[C@H](N)C(=O)Nc1ccc2c(c1)oc(=O)c1cnccc12]

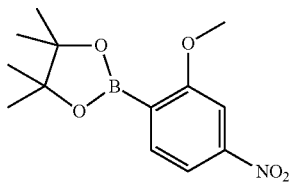 [SMILES: COc1cc([N+](=O)[O-])ccc1B1OC(C)(C)C(C)(C)O1]

Part A. 2-(2-methoxy-4-nitrophenyl)-4,4,5,5-tetramethyl-1,3,2-dioxaborolane

To a suspension of 1-bromo-2-methoxy-4-nitrobenzene (20 g, 86 mmol) in DMSO (100 mL) at room temperature under nitrogen was added Bis(pinacolato)diboron (32.8 g, 129 mmol) and potassium acetate (25.4 g, 259 mmol). The reaction mixture was degassed for 10 min with nitrogen. 1,1'-Bis(diphenylphosphino)ferrocenepalladium(II) dichloride (3.55 g, 4.31 mmol) was added and the reaction mixture was heated at 90° C. for 12 h. The reaction mixture was filtered through diatomaceous earth (Celite®). The filtrate was diluted with water (100 mL) and extracted with ethyl acetate (3×500 mL). The organic layers were combined and washed with brine (1×100 mL), dried (MgSO$_4$), filtered and concentrated under reduced pressure. The residue was purified by silica gel chromatography (hexanes, ethyl acetate) to obtain 2-(2-methoxy-4-nitrophenyl)-4,4,5,5-tetramethyl-1,3,2-dioxaborolane (15.28 g, 54.7 mmol, 64% yield) as brown solid. The parent ion was not observed in the MS. $^1$H NMR (400 MHz, CHLOROFORM-d) δ 7.79 (d, J=1.0 Hz, 2H), 7.67 (s, 1H), 3.93 (s, 3H), 1.38 (s, 12H).

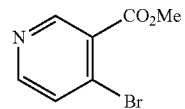

Part B. methyl 4-bromonicotinate

To a solution of 4-bromonicotinic acid (2.81 g, 13.91 mmol) in CH$_2$Cl$_2$ (20 mL) at room temperature under a nitrogen atmosphere was added oxalyl chloride (3.04 mL, 34.8 mmol) followed by dropwise addition of DMF (0.33 mL). Bubbling was observed and the reaction mixture was stirred at room temperature for 45 min. The solution was cooled to 0° C. and methanol (5.63 mL, 139 mmol) was added over 5 min then stirred for 10 min. The solution was concentrated under reduced pressure and the residue taken up in EtOAc and basified with saturated aqueous sodium bicarbonate. The solution was extracted with EtOAc (3×20 mL). The combined organics were washed with brine (1×20 mL), dried (MgSO$_4$), filtered, and concentrated under reduced pressure to obtain methyl 4-bromonicotinate (2.7 g, 11.87 mmol, 85% yield) as a brown oil which was carried on without further purification. $^1$H NMR (400 MHz, CHLOROFORM-d) δ 9.05 (s, 1H), 8.60 (d, J=5.5 Hz, 1H), 7.55-7.32 (m, 1H), 4.03-3.95 (m, 3H); LCMS (ESI) m/e 216.1, 218.1 Br pattern [(M+H)$^+$, calcd for $C_7H_7BrNO_2$ 216.0].

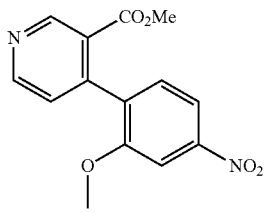 [SMILES: COC(=O)c1cnccc1-c1ccc([N+](=O)[O-])cc1OC]

Part C. methyl 4-(2-methoxy-4-nitrophenyl)nicotinate

To a sealable flask was added methyl 4-bromonicotinate (1.35 g, 6.25 mmol), cesium carbonate (4.07 g, 12.50 mmol), palladium(0)tetrakistriphenyl phosphine (0.722 g, 0.625 mmol) and 2-(2-methoxy-4-nitrophenyl)-4,4,5,5-tetramethyl-1,3,2-dioxaborolane (1.744 g, 6.25 mmol). Dioxane (14.7 mL) and water (3.68 mL) which had been degassed by bubbling nitrogen through the solution for 5 min were added and the vial sealed. The solution was heated to 80° C. in an oil bath for 5 h. The mixture was cooled to room temperature, filtered through diatomaceous earth (Celite®), and concentrated under reduced pressure. The residue was purified via silica gel chromatography (EtOAc: hexanes) to obtain methyl 4-(2-methoxy-4-nitrophenyl) nicotinate (1.9 g, 5.93 mmol, 95% yield) as a brown oil. $^1$H NMR (400 MHz, CHLOROFORM-d) δ 9.15 (d, J=0.5 Hz, 1H), 8.82 (d, J=5.0 Hz, 1H), 7.98 (dd, J=8.3, 2.0 Hz, 1H), 7.79 (d, J=2.0 Hz, 1H), 7.38 (d, J=8.3 Hz, 1H), 7.24 (dd, J=5.0, 0.5 Hz, 1H), 3.84 (s, 3H), 3.76 (s, 3H); LCMS (ESI) m/e 289.1 [(M+H)$^+$, calcd for $C_{14}H_{13}N_2O_5$ 289.1].

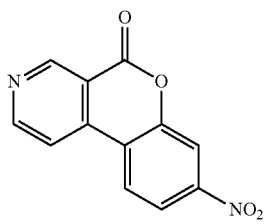

Part D. 8-nitro-5H-chromeno[3,4-c]pyridin-5-one

To methyl 4-(2-methoxy-4-nitrophenyl)nicotinate (1.71 g, 5.93 mmol) in DCM (29.7 ml) at 0° C. was added boron tribromide (2.242 ml, 23.72 mmol) dropwise. The solution was warmed to room temperature and stirred for 14 h. The solution was cooled to 0° C. and quenched with methanol (~10 mL). The solid formed was collected by vacuum filtration. Obtained 8-nitro-5H-chromeno[3,4-c]pyridin-5-one (1.43 g, 5.61 mmol, 95% yield) as a light brown amorphous solid which was carried on without further purification. LCMS (ESI) m/e 243.1, [(M+H)$^+$, calcd for $C_{12}H_7N_2O_4$ 243.0].

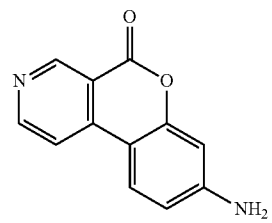 [SMILES: O=c1oc2cc([N+](=O)[O-])ccc2c2ccncc12]

Part E. 8-amino-5H-chromeno[3,4-c]pyridin-5-one

A solution of 8-nitro-5H-chromeno[3,4-c]pyridin-5-one, hydrobromide (800 mg, 2.476 mmol) and palladium on carbon (10% by wt) (26.3 mg, 0.248 mmol) in EtOH (2.4 mL) was shaken under 40 psi H2 for 1.5 h. The mixture was filtered through diatomaceous earth (Celite®) and the filtrate concentrated under reduced pressure. Obtained 8-amino-5H-chromeno[3,4-c]pyridin-5-one, TFA (632 mg, 1.84 mmol, 74% yield) as an orange amorphous solid. LCMS (ESI) m/e 213.2, [(M+H)$^+$, calcd for $C_{12}H_9N_2O_2$ 213.1].

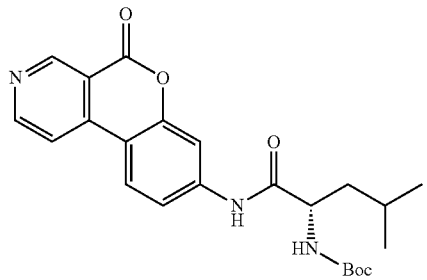 [SMILES: CC(C)C[C@H](NC(=O)OC(C)(C)C)C(=O)Nc1ccc2c(c1)oc(=O)c1cnccc12]

Part F. (S)-tert-butyl (4-methyl-1-oxo-1-((5-oxo-5H-chromeno[3,4-c]pyridin-8-yl)amino)pentan-2-yl) carbamate To a solution of 8-amino-5H-chromeno[3,4-c]pyridin-5-one, TFA (63 mg, 0.193 mmol), (S)-2-((tert-butoxycarbonyl) amino)-4-methylpentanoic acid, water (53.0 mg, 0.212 mmol) and DIEA (169 μl, 0.966 mmol) in DCM (3862 μl) cooled to 0° C. was added HATU (110 mg, 0.290 mmol). The solution was allowed to warm to room temperature and stirred for 12 h. The reaction mixture was concentrated under reduced pressure and the residue was purified by reverse phase HPLC (10%-100% MeOH/H2O/0.1% TFA). Obtained (S)-tert-butyl (4-methyl-1-oxo-1-((5-oxo-5H-chromeno[3,4-c]pyridin-8-yl)amino)pentan-2-yl)carbamate, 2TFA (17 mg, 0.028 mmol, 15% yield) as a pale brown solid. $^1$H NMR (400 MHz, METHANOL-d4) δ 9.41 (br. s., 1H), 8.91 (br. s., 1H), 8.34-8.23 (m, 2H), 7.91 (d, J=2.3 Hz, 1H), 7.62 (d, J=8.8 Hz, 1H), 4.34-4.22 (m, 1H), 1.88-1.72 (m, 2H), 1.46 (d, J=7.5 Hz, 9H), 1.00 (dd, J=6.7, 1.4 Hz, 6H); LCMS (ESI) m/e 426.2 [(M+H)+, calcd for $C_{23}H_{28}N_3O_5$ 426.2].

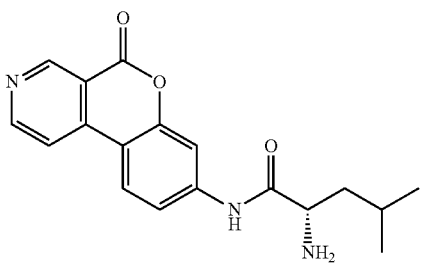 [SMILES: CC(C)C[C@H](N)C(=O)Nc1ccc2c(c1)oc(=O)c1cnccc12]

Part G. (S)-2-amino-4-methyl-N-(5-oxo-5H-chromeno[3,4-c]pyridin-8-yl)pentanamide A solution of (S)-tert-butyl (4-methyl-1-oxo-1-((5-oxo-5H-chromeno[3,4-c]pyridin-8-yl)amino)pentan-2-yl)carbamate, 2TFA (6 mg, 0.014 mmol) in hydrogen chloride (2N in diethyl ether) (176 μl, 0.353 mmol) was stirred at room temperature for 2 h. The mixture was concentrated under reduced pressure and the residue purified by reverse phase HPLC (5%-70% MeOH/H$_2$O/0.1% TFA). Obtained (S)-2-amino-4-methyl-N-(5-oxo-5H-chromeno[3,4-c]pyridin-8-yl)pentanamide (3.4 mg, 5.84 μM, 41% yield) as a yellow film. $^1$H NMR (400 MHz, METHANOL-d$_4$) δ 9.41 (s, 1H), 8.91 (d, J=5.5 Hz, 1H), 8.33 (d, J=8.8 Hz, 1H), 8.28 (d, J=5.5 Hz, 1H), 7.95 (d, J=2.3 Hz, 1H), 7.62 (dd, J=8.8, 2.0 Hz, 1H), 4.09 (t, J=7.2 Hz, 1H), 1.87-1.81 (m, 2H), 1.82-1.75 (m, 1H), 1.07 (d, J=2.3 Hz, 3H), 1.06 (d, J=2.5 Hz, 3H); LCMS (ESI) m/e 326.2 [(M+H)+, calcd for C$_{18}$H$_{20}$N$_3$O$_3$ 326.2].

Example 12 neopentyl 5H-chromeno[3,4-c]pyridin-8-ylcarbamate

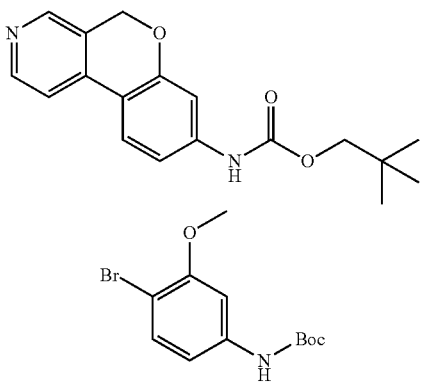

Part A. tert-butyl (4-bromo-3-methoxyphenyl)carbamate

To a stirred solution of 4-bromo-3-methoxyaniline (50 g, 247 mmol) in THF (1.5 L) was added BOC$_2$O (0.069 L, 297 mmol) and triethylamine (0.045 L, 322 mmol) then the resulting reaction mixture was heated to reflux for 12 h. The reaction was cooled to room temperature and the THF was removed under reduced pressure. The residue was taken up in ethyl acetate (500 mL) and washed with water (250 mL) and brine (250 mL) then dried over anhydrous sodium sulfate and concentrated under reduced pressure. The residue was purified by silica gel chromatography (petroleum ether/ethyl acetate) to give tert-butyl (4-bromo-3-methoxyphenyl)carbamate (60 g, 193 mmol, 78% yield) as a light brown solid. $^1$H NMR (400 MHz, DMSO-d$_6$) δ 9.48 (s, 1H), 7.40 (d, J=8.4 Hz, 1H), 7.37 (d, J=2.4 Hz, 1H), 6.96 (dd, J=8.4 Hz, J=2.4 Hz, 1H), 3.79 (s, 3H), 1.48 (s, 9H); LCMS (Method E) (ESI) m/e 302.0, 304.0 Br pattern [(M+H)$^+$, calcd for C$_{12}$H$_{17}$BrNO$_3$ 302.0].

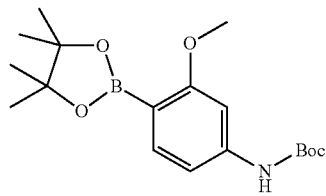 [SMILES: COc1cc(NC(=O)OC(C)(C)C)ccc1B1OC(C)(C)C(C)(C)O1]

Part B. tert-butyl (3-methoxy-4-(4,4,5,5-tetramethyl-1,3,2-dioxaborolan-2-yl)phenyl)carbamate To a stirred solution of tert-butyl (4-bromo-3-methoxyphenyl)carbamate (25 g, 83 mmol) DMF (750 mL) was purged by N2 for 10 min then potassium acetate (24.36 g, 248 mmol) and 4,4,4',4',5,5,5',5'-octamethyl-2,2'-bi(1,3,2-dioxaborolane) (31.5 g, 124 mmol) were added as single portion. The solution was purged with nitrogen for 10 min and then PdCl$_2$(dppf)-CH$_2$Cl$_2$ adduct (6.76 g, 8.27 mmol) was added and the solution purged one more time with N2 for 5 min. The reaction mixture was then heated at 100° C. for 12 h. The mixture was cooled to room temperature and the DMF was removed under reduced pressure. The residue was taken up in ethyl acetate (800 mL) and washed with water (200 mL), brine (200 mL), dried over anhydrous sodium sulfate, and concentrated under reduced pressure to get a brownish oil. The crude material was purified by silica gel chromatography (petroleum ether/ethyl acetate) to give. tert-butyl (3-methoxy-4-(4,4,5,5-tetramethyl-1,3,2-dioxaborolan-2-yl)phenyl)carbamate. $^1$H NMR (400 MHz, DMSO-d$_6$) δ 9.45 (s, 1H), 7.42 (d, J=8.0 Hz, 1H), 7.17 (d, J=1.6 Hz, 1H), 7.00 (dd, J=8.0 Hz, J=1.6 Hz, 1H), 3.66 (s, 3H), 1.47 (s, 9H), 1.24 (s, 12H).

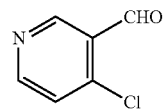

Part C. 4-chloronicotinaldehyde

To a stirred solution of diisopropyl amine (18.83 mL, 132 mmol) in dry THF (150 mL) at −78° C. was added N-butyllithium (7.33 g, 114 mmol) dropwise. After complete addition the reaction temperature was brought to 0° C. and the solution stirred for 1 h. The reaction was brought back to −78° C. and 4-chloropyridine (10 g, 88 mmol) in THF (100 ml) was added over 15 min. After complete addition the reaction mixture was stirred for 1 h at −78° C., then DMF (20 mL) was added and the reaction mixture was stirred for 30 min at room temperature. The reaction mixture was carefully quenched with water (100 mL) and extracted with ethyl acetate (3×150 mL). The combined organics were washed with water (100 mL), brine (100 mL), dried over anhydrous sodium sulfate, and concentrated under reduced pressure. The residue was purified by silica gel chromatography (petroleum ether/ethyl acetate) to afford 4-chloronicotinaldehyde (8.0 g, 56.5 mmol, 64% yield) as colorless solid. $^1$H NMR (400 MHz, CDCl$_3$) δ 10.51 (s, 1H), 9.05 (s, 1H), 8.68 (d, J=5.6 Hz, 1H), 7.44 (d, J=5.6 Hz, 1H); LCMS (ESI) m/e 142.2 [(M+H)$^+$, calcd for C$_6$H$_5$ClNO 142.0].

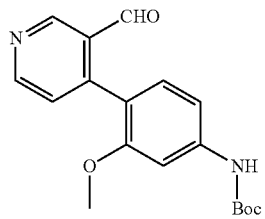 [SMILES: COc1cc(NC(=O)OC(C)(C)C)ccc1-c1ccncc1C=O]

Part D. tert-butyl (4-(3-(hydroxymethyl)pyridin-4-yl)-3-methoxyphenyl)carbamate

A stirred solution of tert-butyl (3-methoxy-4-(4,4,5,5-tetramethyl-1,3,2-dioxaborolan-2-yl)phenyl)carbamate (12.95 g, 37.1 mmol) in 1,4-dioxane (300 mL) and water (50 mL) was purged with nitrogen for 10 min. 4-Chloronicotinaldehyde (5 g, 35.3 mmol) and potassium phosphate, tribasic (30.0 g, 141 mmol) was added and the solution again degassed with N2 for 5 min. PdCl$_2$(dppf)-CH$_2$Cl$_2$ adduct (2.308 g, 2.83 mmol) was added and the solution again degassed with N$_2$ for 5 min. The reaction mixture was heated at 100° C. for 1 h under a nitrogen atmosphere. The mixture was cooled to room temperature and quenched with water (100 mL) and extracted with ethyl acetate (3×150 mL). The combined organic layers were washed with water (100 mL), brine (100 mL), dried over anhydrous sodium sulfate, then concentrated under reduced pressure. The crude material was purified by silica gel chromatography (petroleum ether/ ethyl acetate), to afford tert-butyl (4-(3-formylpyridin-4-yl)-3-methoxyphenyl)carbamate (9.0 g, 27.4 mmol, 78% yield) as colorless solid. $^1$H NMR (300 MHz, DMSO-d$_6$) δ 9.74 (s, 1H), 9.63 (s, 1H), 8.89 (s, 1H), 8.79 (d, J=5.1 Hz, 1H), 7.41 (dd, J=7.2 Hz, J=2.1 Hz, 1H), 7.29 (d, J=8.4 Hz, 1H), 7.18 (dd, J=8.4 Hz, J=2.1 Hz, 1H), 3.67 (s, 3H), 1.50 (s, 9H); LCMS (ESI) m/e 329.2 [(M+H)$^+$, calcd for C$_{18}$H$_{21}$N$_2$O$_4$ 329.2].

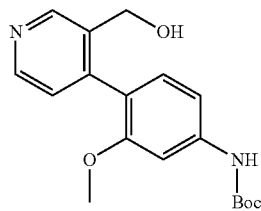 [SMILES: COc1cc(NC(=O)OC(C)(C)C)ccc1-c1ccncc1CO]

Part E. tert-butyl (4-(3-(hydroxymethyl)pyridin-4-yl)-3-methoxyphenyl)carbamate

To a stirred solution of tert-butyl (4-(3-formylpyridin-4-yl)-3-methoxyphenyl)carbamate (8.0 g, 24.36 mmol) in methanol (140 mL) was added sodium borohydride (1.11 g, 29.2 mmol) at 0° C. under N$_2$. After complete addition the resulting mixture was stirred at room temperature for 1 h. The reaction mixture was quenched with water (150 mL), the methanol was removed under reduced pressure, and the solution was extracted with ethyl acetate (2×200 mL). The combined organic layers were washed with water (100 mL), brine (100 mL), dried over sodium sulfate and concentrated under reduced pressure. The crude solid was washed with hot 50% ethyl acetate in petroleum ether (50 mL) and the solid collected by vacuum filtration to afford tert-butyl (4-(3-(hydroxymethyl)pyridin-4-yl)-3-methoxyphenyl)carbamate (6.0 g, 17.8 mmol, 73% yield) an off-white solid. $^1$H NMR (300 MHz, DMSO-d$_6$) δ 9.50 (s, 1H), 8.67 (s, 1H), 8.42 (d, J=4.8 Hz, 1H), 7.37 (d, J=1.2 Hz, 1H), 7.11-7.02 (m, 3H), 5.13 (d, J=5.4 Hz, 1H), 4.32 (d, J=5.4 Hz, 2H), 3.67 (s, 3H), 1.49 (s, 9H).

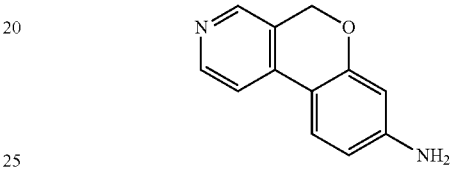

Part F. 5H-chromeno[3,4-c]pyridin-8-amine

To a solution of tert-butyl (4-(3-(hydroxymethyl)pyridin-4-yl)-3-methoxyphenyl)carbamate (5.0 g, 15.13 mmol) in water (0.822 ml, 15.13 mmol) was added hydrobromic acid (63%) then the solution was heated at 100° C. for 14 h. The reaction mixture was concentrated under reduced pressure. The residue was taken in up in DCM (100 mL) and water (100 mL) then basified with 1N sodium hydroxide. The solution was extracted with DCM (2×300 mL). The combined organic layers were washed with water (100 mL), brine (100 mL), dried over sodium sulfate, and concentrated under reduced pressure. The crude solid was washed with 20% of ethyl acetate in petroleum ether and dried under vacuum to afford 5H-chromeno[3,4-c]pyridin-8-amine (2.0 g, 9.99 mmol, 66% yield) a yellow solid. $^1$H NMR (400 MHz, DMSO-d$_6$) δ 8.40 (d, J=5.2 Hz, 1H), 8.31 (s, 1H), 7.57 (d, J=6.3 Hz, 1H), 7.51 (d, J=5.2 Hz, 1H), 6.33 (dd, J=8.4 Hz, J=2.0 Hz, 1H), 6.15 (d, J=2.0 Hz, 1H), 5.06 (s, 2H).

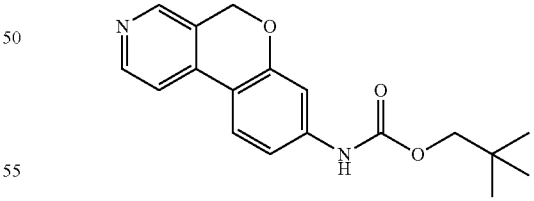

Part G. neopentyl 5H-chromeno[3,4-c]pyridin-8-ylcarbamate

To a solution of 5H-chromeno[3,4-c]pyridin-8-amine (13.8 mg, 0.069 mmol) in DCE (1 mL) was added DIEA (48 µL, 0.277 mmol) and neopentyl chloroformate (21 µL, 1.39 mmol). The mixture was stirred at room temperature for 12 h. The reaction was concentrated under reduced pressure and purified via reverse phase HPLC (acetonitrile:water with 20-mM ammonium-hydroxide). Obtained neopentyl 5H-chromeno[3,4-c]pyridin-8-ylcarbamate (16.5 mg, 0.053 mmol, 77% yield). $^1$H NMR (500 MHz, DMSO-$d_6$) δ 9.87 (s, 1H), 8.51 (d, J=5.2 Hz, 1H), 8.42 (s, 1H), 7.85 (d, J=8.5 Hz, 1H), 7.69 (d, J=5.2 Hz, 1H), 7.23 (s, 1H), 7.20 (d, J=8.5 Hz, 1H), 5.17 (s, 2H), 3.81 (s, 2H), 0.94 (s, 9H); LCMS (ESI) m/e 313.3 [(M+H)$^+$, calcd for $C_{18}H_{21}N_3O_3$ 313.2].

Example 13

1-(5H-chromeno[3,4-c]pyridin-8-yl)-3-cyclohexylurea

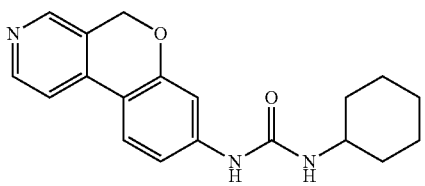 [SMILES: O=C(Nc1ccc2c(c1)OCc1cnccc1-2)NC1CCCCC1]

The title compound was prepared following the same protocol described in Example 12 using cyclohexylcarbamic chloride (22.3 mg, 1.39 mmol) in Part G to give 1-(5H-chromeno[3,4-c]pyridin-8-yl)-3-cyclohexylurea (2.7 mg, 8.35 μmol, 12% yield). $^1$H NMR (500 MHz, DMSO-$d_6$) δ 8.62 (s, 1H), 8.48 (d, J=5.5 Hz, 1H), 8.39 (s, 1H), 7.78 (d, J=8.9 Hz, 1H), 7.65 (d, J=5.2 Hz, 1H), 7.22 (s, 1H), 7.00 (d, J=8.5 Hz, 1H), 6.19 (d, J=7.9 Hz, 1H), 5.14 (s, 2H), 3.48-3.30 (m, 1H), 1.85-1.42 (m, 4H), 1.36-0.95 (m, 6H); LCMS (ESI) m/e 324.3 [(M+H)$^+$, calcd for $C_{19}H_{22}N_3O_2$ 324.2].

Example 14

N-(5H-chromeno[3,4-c]pyridin-8-yl)pent-4-ynamide

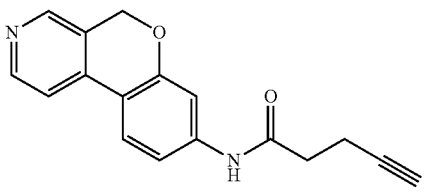 [SMILES: C#CCCC(=O)Nc1ccc2c(c1)OCc1cnccc1-2]

The title compound was prepared following the same protocol described in Example 12 using pent-4-ynoic acid (9.81 mg, 0.100 mmol) to give N-(5H-chromeno[3,4-c]pyridin-8-yl)pent-4-ynamide (9.6 mg, 0.034 mmol, 69% yield). $^1$H NMR (500 MHz, DMSO-$d_6$) δ 10.22 (s, 1H), 8.53 (d, J=4.9 Hz, 1H), 8.44 (s, 1H), 7.89 (d, J=8.5 Hz, 1H), 7.71 (d, J=4.9 Hz, 1H), 7.42 (s, 1H), 7.28 (d, J=8.2 Hz, 1H), 5.19 (s, 2H), 2.80 (s, 1H), 2.62-2.40 (m, 4H); LCMS (ESI) m/e 279.2 [(M+H)$^+$, calcd for $C_{17}H_{15}N_2O_2$ 279.1].

Example 15

N-(5H-chromeno[3,4-c]pyridin-8-yl)pentanamide

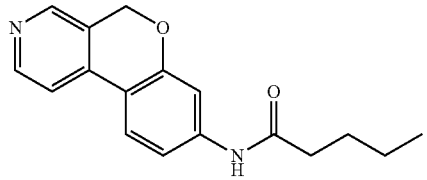 [SMILES: CCCCC(=O)Nc1ccc2c(c1)OCc1cnccc1-2]

The title compound was prepared following the same protocol described in Example 12 using pentanoic acid (10.21 mg, 0.100 mmol) to give N-(5H-chromeno[3,4-c]pyridin-8-yl)pentanamide (13.0 mg, 0.046 mmol, 92% yield). $^1$H NMR (500 MHz, DMSO-$d_6$) δ 10.18 (br. s., 1H), 8.48 (br. s., 1H), 8.39 (br. s., 1H), 7.83 (d, J=8.2 Hz, 1H), 7.68 (br. s., 1H), 7.38 (br. s., 1H), 7.24 (d, J=7.3 Hz, 1H), 5.15 (br. s., 2H), 2.29 (d, J=6.4 Hz, 2H), 1.53 (d, J=6.4 Hz, 2H), 1.28 (d, J=6.7 Hz, 2H), 0.86 (dt, J=7.1, 3.6 Hz, 3H); LCMS (ESI) m/e 283.2 [(M+H)$^+$, calcd for $C_{17}H_{19}N_2O_2$ 283.1].

Example 16

N-(5H-chromeno[3,4-c]pyridin-8-yl)-3-cyanopropanamide

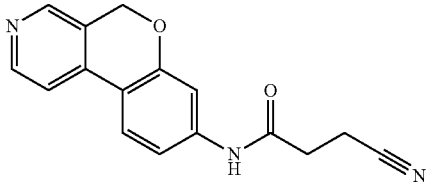 [SMILES: N#CCCC(=O)Nc1ccc2c(c1)OCc1cnccc1-2]

The title compound was prepared following the same protocol described in Example 12 using 3-cyanopropanoic acid (9.91 mg, 0.100 mmol) to give N-(5H-chromeno[3,4-c]pyridin-8-yl)-3-cyanopropanamide (4.1 mg, 0.015 mmol, 29% yield). $^1$H NMR (500 MHz, DMSO-$d_6$) δ 10.34 (s, 1H), 8.53 (d, J=4.9 Hz, 1H), 8.44 (s, 1H), 7.90 (d, J=8.2 Hz, 1H), 7.71 (d, J=5.2 Hz, 1H), 7.40 (s, 1H), 7.27 (d, J=8.2 Hz, 1H), 5.19 (s, 2H), 2.73 (s, 4H); LCMS (ESI) m/e 280.1 [(M+H)$^+$, calcd for $C_{16}H_{14}N_3O_2$ 280.1].

Example 17

N-(5H-chromeno[3,4-c]pyridin-8-yl)acetamide

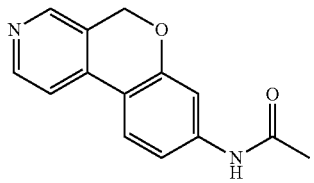 [SMILES: CC(=O)Nc1ccc2c(c1)OCc1cnccc1-2]

The title compound was prepared following the same protocol described in Example 12 using acetic acid (6.00 mg, 0.100 mmol) to give N-(5H-chromeno[3,4-c]pyridin-8-yl)acetamide (9.4 mg, 0.039 mmol, 78% yield). $^1$H NMR (500 MHz, DMSO-$d_6$) δ 10.16 (br. s., 1H), 8.52 (d, J=5.2 Hz, 1H), 8.44 (s, 1H), 7.91-7.83 (m, 1H), 7.70 (d, J=5.2 Hz, 1H), 7.40 (d, J=1.8 Hz, 1H), 7.25 (dd, J=8.4, 2.0 Hz, 1H), 5.28-5.03 (m, 2H), 2.19-1.92 (m, 3H); LCMS (ESI) m/e 241.2 [(M+H)$^+$, calcd for $C_{14}H_{13}N_2O_2$ 241.1].

Example 18

N-(5H-chromeno[3,4-c]pyridin-8-yl)-3-methoxypropanamide

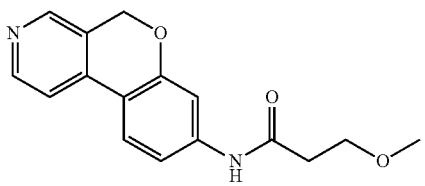 [SMILES: COCCC(=O)Nc1ccc2c(c1)OCc1cnccc1-2]

The title compound was prepared following the same protocol described in Example 12 using 3-methoxypropanoic acid (10.41 mg, 0.100 mmol) to give N-(5H-chromeno[3,4-c]pyridin-8-yl)-3-methoxypropanamide (11.3 mg, 0.040 mmol, 79% yield). $^1$H NMR (500 MHz, DMSO-$d_6$) δ 10.18 (s, 1H), 8.53 (d, J=5.2 Hz, 1H), 8.44 (s, 1H), 7.88 (d, J=8.5 Hz, 1H), 7.71 (d, J=4.9 Hz, 1H), 7.43 (d, J=1.8 Hz, 1H), 7.28 (dd, J=8.5, 1.8 Hz, 1H), 5.19 (s, 2H), 3.62 (t, J=6.1 Hz, 2H), 3.25 (s, 3H), 2.57 (t, J=6.1 Hz, 2H); LCMS (ESI) m/e 285.3 [(M+H)$^+$, calcd for $C_{16}H_{17}N_2O_3$ 285.1].

Example 19

N-(5H-chromeno[3,4-c]pyridin-8-yl)-3-hydroxypropanamide

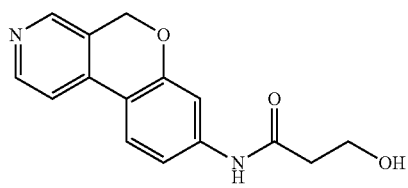 [SMILES: O=C(CCO)Nc1ccc2c(c1)OCc1cnccc1-2]

The title compound was prepared following the same protocol described in Example 12 using 3-hydroxypropanoic acid (9.01 mg, 0.100 mmol) to give N-(5H-chromeno[3,4-c]pyridin-8-yl)-3-hydroxypropanamide (2.3 mg, 8.51 μmol, 17% yield). $^1$H NMR (500 MHz, DMSO-$d_6$) δ 10.15 (s, 1H), 8.53 (d, J=5.2 Hz, 1H), 8.44 (s, 1H), 7.88 (d, J=8.5 Hz, 1H), 7.71 (d, J=5.2 Hz, 1H), 7.45 (s, 1H), 7.29 (d, J=8.5 Hz, 1H), 5.19 (s, 2H), 4.74 (br. s., 1H), 3.72 (t, J=5.6 Hz, 2H), 2.49-2.45 (m, 2H); LCMS (ESI) m/e 271.2 [(M+H)$^+$, calcd for $C_{15}H_{15}N_2O_3$ 271.1].

Example 20

N-(5H-chromeno[3,4-c]pyridin-8-yl)-1-cyanocyclopropanecarboxamide

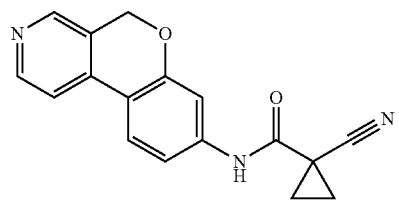 [SMILES: N#CC1(C(=O)Nc2ccc3c(c2)OCc2cnccc2-3)CC1]

The title compound was prepared following the same protocol described in Example 12 using 1-cyanocyclopropanecarboxylic acid (11.11 mg, 0.100 mmol) to give N-(5H-chromeno[3,4-c]pyridin-8-yl)-1-cyanocyclopropanecarboxamide (6.3 mg, 0.022 mmol, 43% yield). $^1$H NMR (500 MHz, DMSO-$d_6$) δ 10.20 (br. s., 1H), 8.55 (d, J=4.9 Hz, 1H), 8.46 (s, 1H), 7.92 (d, J=7.9 Hz, 1H), 7.74 (d, J=4.9 Hz, 1H), 7.41-7.34 (m, 2H), 5.21 (s, 2H), 1.70 (s, 4H); LCMS (ESI) m/e 292.2 [(M+H)$^+$, calcd for $C_{17}H_{14}N_3O_2$ 292.1].

Example 21

N-(5H-chromeno[3,4-c]pyridin-8-yl)-4-sulfamoylbutanamide

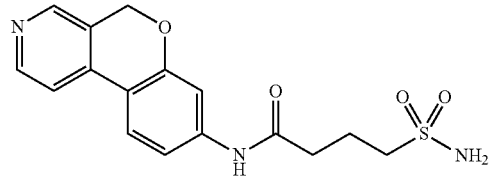 [SMILES: NS(=O)(=O)CCCC(=O)Nc1ccc2c(c1)OCc1cnccc1-2]

The title compound was prepared following the same protocol described in Example 12 using 4-sulfamoylbutanoic acid (16.72 mg, 0.100 mmol) to give N-(5H-chromeno[3,4-c]pyridin-8-yl)-4-sulfamoylbutanamide (2.7 mg, 7.77 μmol, 16% yield). $^1$H NMR (500 MHz, DMSO-$d_6$) δ 10.20 (br. s., 1H), 8.53 (d, J=4.9 Hz, 1H), 8.44 (s, 1H), 7.88 (d, J=8.2 Hz, 1H), 7.71 (d, J=5.2 Hz, 1H), 7.43 (s, 1H), 7.28 (d, J=8.2 Hz, 1H), 6.82 (br. s., 2H), 5.19 (s, 2H), 3.10-2.99 (m, 2H), 2.54-2.52 (m, 2H), 2.06-1.95 (m, 2H); LCMS (ESI) m/e 348.2 [(M+H)$^+$, calcd for $C_{16}H_{18}N_3O_4S$ 348.1].

Example 22

N-(5H-chromeno[3,4-c]pyridin-8-yl)-3-(2-oxopyrrolidin-1-yl)propanamide

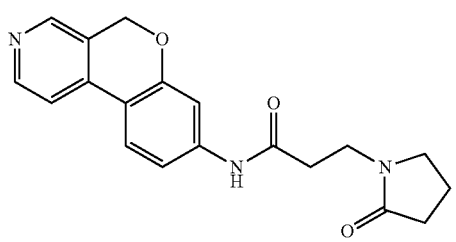 [SMILES: O=C(CCN1CCCC1=O)Nc1ccc2c(c1)OCc1cnccc1-2]

The title compound was prepared following the same protocol described in Example 12 using 3-(2-oxopyrrolidin-1-yl)propanoic acid (15.72 mg, 0.100 mmol) to give N-(5H-chromeno[3,4-c]pyridin-8-yl)-3-(2-oxopyrrolidin-1-yl)propanamide (11.9 mg, 0.035 mmol, 71% yield). $^1$H NMR (500 MHz, DMSO-$d_6$) δ 10.23 (s, 1H), 8.53 (d, J=5.2 Hz, 1H), 8.45 (s, 1H), 7.89 (d, J=8.2 Hz, 1H), 7.71 (d, J=5.5 Hz, 1H), 7.41 (d, J=1.8 Hz, 1H), 7.26 (dd, J=8.4, 2.0 Hz, 1H), 5.19 (s, 2H), 3.48 (t, J=6.9 Hz, 2H), 3.35-3.31 (m, 2H), 2.55 (t, J=7.0 Hz, 2H), 2.23-2.17 (m, 2H), 1.90 (quin, J=7.6 Hz, 2H); LCMS (ESI) m/e 338.3 [(M+H)$^+$, calcd for $C_{19}H_{20}N_3O_3$ 338.2].

Example 23

N-(5H-chromeno[3,4-c]pyridin-8-yl)cyclohexanecarboxamide

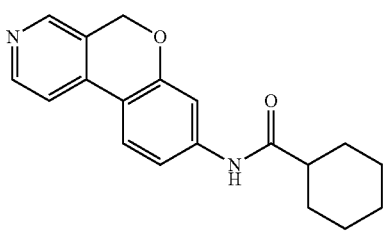 [SMILES: O=C(Nc1ccc2c(c1)OCc1cnccc1-2)C1CCCCC1]

The title compound was prepared following the same protocol described in Example 12 using cyclohexanecarboxylic acid (12.82 mg, 0.100 mmol) to give N-(5H-chromeno[3,4-c]pyridin-8-yl)cyclohexanecarboxamide (13.7 mg, 0.044 mmol, 89% yield). $^1$H NMR (500 MHz, DMSO-$d_6$) δ 10.03 (s, 1H), 8.53 (d, J=5.2 Hz, 1H), 8.44 (s, 1H), 7.87 (d, J=8.5 Hz, 1H), 7.70 (d, J=4.9 Hz, 1H), 7.44 (s, 1H), 7.30 (d, J=7.9 Hz, 1H), 5.18 (s, 2H), 2.33 (t, J=11.7 Hz, 1H), 1.88-1.72 (m, 4H), 1.66 (d, J=11.3 Hz, 1H), 1.48-1.35 (m, 2H), 1.32-1.13 (m, 3H); LCMS (ESI) m/e 309.3 [(M+H)$^+$, calcd for $C_{19}H_{21}N_2O_2$ 309.2].

Example 24

N-(5H-chromeno[3,4-c]pyridin-8-yl)isobutyramide

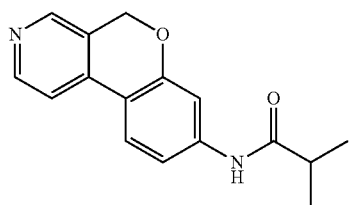 [SMILES: CC(C)C(=O)Nc1ccc2c(c1)OCc1cnccc1-2]

The title compound was prepared following the same protocol described in Example 12 using isobutyric acid (8.81 mg, 0.100 mmol) to give N-(5H-chromeno[3,4-c]pyridin-8-yl)isobutyramide (11.5 mg, 0.043 mmol, 86% yield). $^1$H NMR (500 MHz, DMSO-$d_6$) δ 10.05 (s, 1H), 8.53 (d, J=5.2 Hz, 1H), 8.44 (s, 1H), 7.88 (d, J=8.5 Hz, 1H), 7.71 (d, J=5.2 Hz, 1H), 7.44 (d, J=1.5 Hz, 1H), 7.36-7.23 (m, 1H), 5.19 (s, 2H), 2.60 (quin, J=6.9 Hz, 1H), 1.11 (d, J=6.7 Hz, 6H); LCMS (ESI) m/e 269.2 [(M+H)$^+$, calcd for $C_{16}H_{17}N_2O_2$ 269.1].

Example 25

N-(5H-chromeno[3,4-c]pyridin-8-yl)-2-cyanoacetamide

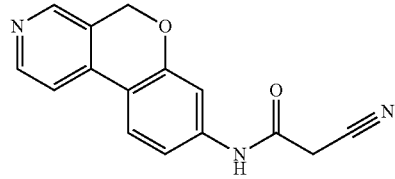 [SMILES: N#CCC(=O)Nc1ccc2c(c1)OCc1cnccc1-2]

The title compound was prepared following the same protocol described in Example 12 using 2-cyanoacetic acid (8.51 mg, 0.100 mmol) to give N-(5H-chromeno[3,4-c]pyridin-8-yl)-2-cyanoacetamide (10.7 mg, 0.040 mmol, 81% yield). $^1$H NMR (500 MHz, DMSO-$d_6$) δ 10.52 (br. s., 1H), 8.55 (d, J=5.2 Hz, 1H), 8.46 (s, 1H), 7.93 (d, J=8.5 Hz, 1H), 7.73 (d, J=4.9 Hz, 1H), 7.35 (s, 1H), 7.24 (d, J=8.2 Hz, 1H), 5.21 (s, 2H), 3.94 (s, 2H); LCMS (ESI) m/e 266.2 [(M+H)$^+$, calcd for $C_{15}H_{12}N_3O_2$ 266.1].

Example 26

N-(5H-chromeno[3,4-c]pyridin-8-yl)-3,3-dimethylbutanamide

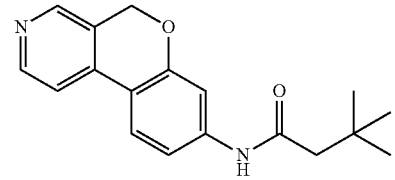

The title compound was prepared following the same protocol described in Example 12 using 3,3-dimethylbutanoic acid (11.61 mg, 0.100 mmol) to give N-(5H-chromeno[3,4-c]pyridin-8-yl)-3,3-dimethylbutanamide (11.4 mg, 0.038 mmol, 77% yield). $^1$H NMR (500 MHz, DMSO-$d_6$) δ 10.01 (s, 1H), 8.53 (d, J=5.2 Hz, 1H), 8.44 (s, 1H), 7.87 (d, J=8.5 Hz, 1H), 7.70 (d, J=4.9 Hz, 1H), 7.44 (s, 1H), 7.28 (d, J=8.5 Hz, 1H), 5.19 (s, 2H), 2.21 (s, 2H) 1.03 (s, 9H); LCMS (ESI) m/e 297.9 [(M+H)$^+$, calcd for $C_{18}H_{21}N_2O_2$ 297.1].

Example 27

N-(5H-chromeno[3,4-c]pyridin-8-yl)-3-methylbutanamide

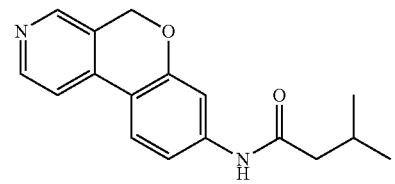 [SMILES: CC(C)CC(=O)Nc1ccc2c(c1)OCc1cnccc1-2]

The title compound was prepared following the same protocol described in Example 12 using 3-methylbutanoic acid (10.21 mg, 0.100 mmol) to give N-(5H-chromeno[3,4-c]pyridin-8-yl)-3-methylbutanamide (11.3 mg, 0.040 mmol, 80% yield). $^1$H NMR (500 MHz, DMSO-d$_6$) δ 10.08 (s, 1H), 8.53 (d, J=5.2 Hz, 1H), 8.44 (s, 1H), 7.88 (d, J=8.5 Hz, 1H), 7.70 (d, J=5.2 Hz, 1H), 7.44 (s, 1H), 7.28 (d, J=8.9 Hz, 1H), 5.19 (s, 2H), 2.21 (d, J=7.0 Hz, 2H), 2.08 (dt, J=13.6, 6.6 Hz, 1H), 1.00-0.82 (m, 6H); LCMS (ESI) m/e 283.2 [(M+H)$^+$, calcd for C$_{17}$H$_{19}$N$_2$O$_2$ 283.1].

Example 28

N-(5H-chromeno[3,4-c]pyridin-8-yl)propionamide

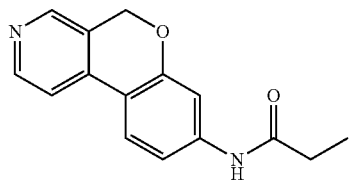 [SMILES: CCC(=O)Nc1ccc2c(c1)OCc1cnccc1-2]

The title compound was prepared following the same protocol described in Example 12 using propionic acid (7.41 mg, 0.100 mmol) to give N-(5H-chromeno[3,4-c]pyridin-8-yl)propionamide (10.0 mg, 0.039 mmol, 79% yield). $^1$H NMR (500 MHz, DMSO-d$_6$) δ 10.08 (br. s., 1H), 8.53 (d, J=4.9 Hz, 1H), 8.44 (s, 1H), 7.88 (d, J=8.5 Hz, 1H), 7.70 (d, J=5.2 Hz, 1H), 7.43 (br. s., 1H), 7.28 (d, J=8.2 Hz, 1H), 5.19 (s, 2H), 2.51 (br. s., 3H), 2.40-2.28 (m, 2H); LCMS (ESI) m/e 255.2 [(M+H)$^+$, calcd for C$_{15}$H$_{15}$N$_2$O$_2$ 255.1].

Example 29 methyl 4-((5H-chromeno[3,4-c]pyridin-8-yl)amino)-4-oxobutanoate

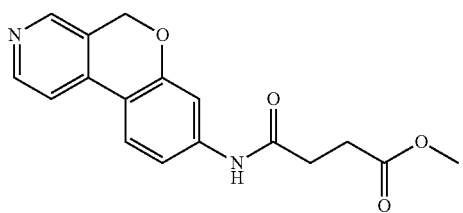 [SMILES: COC(=O)CCC(=O)Nc1ccc2c(c1)OCc1cnccc1-2]

The title compound was prepared following the same protocol described in Example 12 using 4-methoxy-4-oxobutanoic acid (13.21 mg, 0.100 mmol) to give methyl 4-((5H-chromeno[3,4-c]pyridin-8-yl)amino)-4-oxobutanoate (9.7 mg, 0.031 mmol, 62% yield). $^1$H NMR (500 MHz, DMSO-d$_6$) δ 10.22 (s, 1H), 8.53 (d, J=5.2 Hz, 1H), 8.44 (s, 1H), 7.88 (d, J=8.5 Hz, 1H), 7.71 (d, J=5.2 Hz, 1H), 7.40 (s, 1H), 7.27 (d, J=8.2 Hz, 1H), 5.19 (s, 2H), 3.61 (s, 3H), 2.68-2.58 (m, 4H); LCMS (ESI) m/e 313.2 [(M+H)$^+$, calcd for C$_{17}$H$_{17}$N$_2$O$_4$ 313.1].

Example 30

N-(5H-chromeno[3,4-c]pyridin-8-yl)-4-methylpentanamide

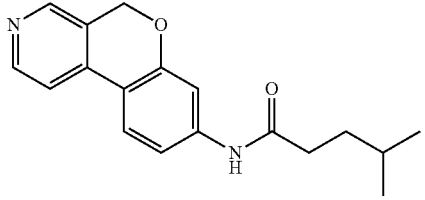 [SMILES: CC(C)CCC(=O)Nc1ccc2c(c1)OCc1cnccc1-2]

The title compound was prepared following the same protocol described in Example 12 using 4-methylpentanoic acid (11.61 mg, 0.100 mmol) to give N-(5H-chromeno[3,4-c]pyridin-8-yl)-4-methylpentanamide (7.2 mg, 0.024 mmol, 49% yield). $^1$H NMR (500 MHz, DMSO-d$_6$) δ 10.10 (br. s., 1H), 8.52 (d, J=5.2 Hz, 1H), 8.44 (s, 1H), 7.87 (dd, J=8.5, 3.1 Hz, 1H), 7.73-7.67 (m, 1H), 7.42 (d, J=2.1 Hz, 1H), 7.27 (dd, J=8.4, 2.0 Hz, 1H), 5.19 (d, J=3.1 Hz, 2H), 2.38-2.27 (m, 2H), 1.56 (dt, J=13.3, 6.5 Hz, 1H), 1.53-1.44 (m, 2H), 0.90 (dd, J=6.4, 3.1 Hz, 6H); LCMS (ESI) m/e 297.3 [(M+H)$^+$, calcd for C$_{18}$H$_{21}$N$_2$O$_2$ 297.2].

Example 31

N-(5H-chromeno[3,4-c]pyridin-8-yl)butyramide

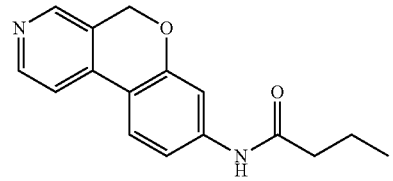

The title compound was prepared following the same protocol described in Example 12 using butyric acid (8.81 mg, 0.100 mmol) to give N-(5H-chromeno[3,4-c]pyridin-8-yl)butyramide (10.9 mg, 0.041 mmol, 81% yield). $^1$H NMR (500 MHz, DMSO-d$_6$) δ 10.10 (s, 1H), 8.53 (d, J=5.2 Hz, 1H), 8.44 (s, 1H), 7.87 (d, J=8.5 Hz, 1H), 7.70 (d, J=5.2 Hz, 1H), 7.43 (s, 1H), 7.28 (d, J=7.6 Hz, 1H), 5.18 (s, 2H), 2.51 (br. s., 4H), 2.31 (t, J=7.3 Hz, 2H), 1.72-1.44 (m, 2H); LCMS (ESI) m/e 269.2 [(M+H)$^+$, calcd for C$_{16}$H$_{17}$N$_2$O$_2$ 269.1].

Example 32

N-(5H-chromeno[3,4-c]pyridin-8-yl)pivalamide

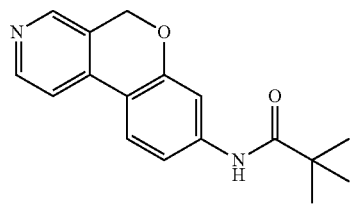 [SMILES: CC(C)(C)C(=O)Nc1ccc2c(c1)OCc1cnccc1-2]

The title compound was prepared following the same protocol described in Example 12 using pivalic acid (5.11 mg, 0.050 mmol) to give N-(5H-chromeno[3,4-c]pyridin-8-yl)pivalamide (8.2 mg, 0.029 mmol, 58% yield). $^1$H NMR (500 MHz, DMSO-$d_6$) δ 9.37 (s, 1H), 8.53 (d, J=5.2 Hz, 1H), 8.44 (s, 1H), 7.88 (d, J=8.5 Hz, 1H), 7.72 (d, J=4.9 Hz, 1H), 7.49 (s, 1H), 7.43 (d, J=8.5 Hz, 1H), 5.19 (s, 2H), 1.24 (s, 9H); LCMS (ESI) m/e 283.0 [(M+H)$^+$, calcd for $C_{17}H_{19}N_2O_2$ 283.1].

Example 33

N-(5H-chromeno[3,4-c]pyridin-8-yl)-2-(dimethylamino)acetamide

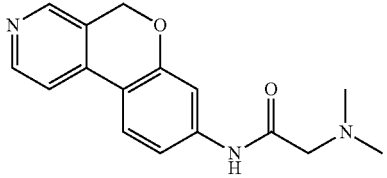 [SMILES: CN(C)CC(=O)Nc1ccc2c(c1)OCc1cnccc1-2]

The title compound was prepared following the same protocol described in Example 12 using 2-(dimethylamino)acetic acid (5.16 mg, 0.050 mmol) to give N-(5H-chromeno[3,4-c]pyridin-8-yl)-2-(dimethylamino)acetamide (8.3 mg, 0.029 mmol, 59% yield). $^1$H NMR (500 MHz, DMSO-$d_6$) δ 9.96 (br. s., 1H), 8.52 (d, J=4.9 Hz, 1H), 8.43 (s, 1H), 7.87 (d, J=8.5 Hz, 1H), 7.71 (d, J=5.2 Hz, 1H), 7.48 (d, J=1.8 Hz, 1H), 7.37 (dd, J=8.5, 1.8 Hz, 1H), 5.18 (s, 2H), 3.08 (s, 2H), 2.26 (s, 6H); LCMS (ESI) m/e 284.2 [(M+H)$^+$, calcd for $C_{16}H_{18}N_3O_2$ 284.1].

Example 34

N-(9-bromo-5H-chromeno[3,4-c]pyridin-8-yl)pentanamide

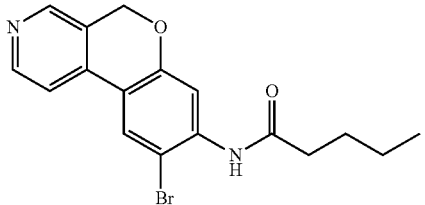 [SMILES: CCCCC(=O)Nc1cc2c(cc1Br)-c1ccncc1CO2]

A mixture of N-(5H-chromeno[3,4-c]pyridin-8-yl)pentanamide (10 mg, 0.035 mmol) and 1-bromopyrrolidine-2,5-dione (6.93 mg, 0.039 mmol) in acetonitrile (708 μl) was heated to 90° C. for 1 h. The mixture was cooled to room temperature and purified via silica gel chromatography (EtOAc in hexanes) to afford N-(9-bromo-5H-chromeno[3,4-c]pyridin-8-yl)pentanamide (6 mg, 0.016 mmol, 45.5% yield) as a colorless solid. $^1$H NMR (400 MHz, METHANOL-$d_4$) δ 8.51 (d, J=5.5 Hz, 1H), 8.41 (s, 1H), 8.15 (s, 1H), 7.74 (d, J=5.5 Hz, 1H), 7.57 (s, 1H), 5.22 (s, 2H), 4.63 (s, 1H), 2.49 (t, J=7.5 Hz, 2H), 1.78-1.66 (m, 2H), 1.45 (dq, J=7.5, 7.3 Hz, 2H), 0.99 (t, J=7.3 Hz, 3H); LCMS (ESI) m/e 361.1, 363.1 Br pattern [(M+H)$^+$, calcd for $C_{17}H_{18}BrN_2O_2$ 361.1].

Example 35

(S)—N-(2-acetamido-5H-chromeno[3,4-c]pyridin-8-yl)-2-amino-4-methylpentanamide

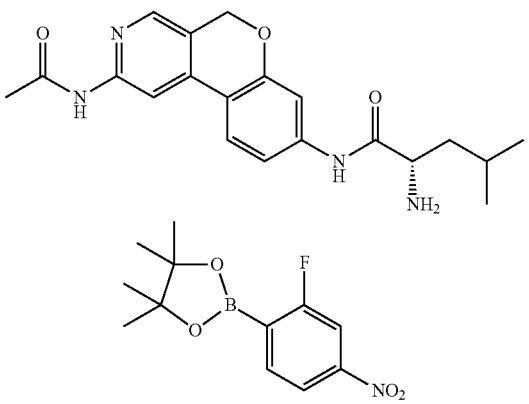

Part A. 2-(2-fluoro-4-nitrophenyl)-4,4,5,5-tetramethyl-1,3,2-dioxaborolane

A solution of 2-fluoro-1-iodo-4-nitrobenzene (2 g, 7.49 mmol), potassium acetate (2.205 g, 22.47 mmol), and bis(pinacolato)diboron (2.283 g, 8.99 mmol), in dioxane (21.10 ml) was purged with $N_2$ gas for 5 min. 1,1'-Bis(diphenylphosphino)ferrocenepalladium(II) dichloride, toluene (0.616 g, 0.749 mmol) was added and the solution was again purged with $N_2$ gas for 5 min. The mixture was heated in an oil bath at 80° C. for 2 h. The brown mixture was cooled to room temperature and filtered through diatomaceous earth (Celite®) eluting with EtOAc. The residue was purified via silica gel chromatography (10%-20% EtOAc in hexanes). Obtained 2-(2-fluoro-4-nitrophenyl)-4,4,5,5-tetramethyl-1,3,2-dioxaborolane (1.3 g, 4.87 mmol, 65% yield) as a pale yellow solid. $^1$H NMR (400 MHz, METHANOL-$d_4$) δ 8.07-8.04 (m, 1H), 7.97-7.91 (m, 1H), 7.78-7.70 (m, 1H), 1.21 (s, 12H).

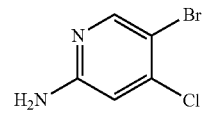

Part B. 5-bromo-4-chloropyridin-2-amine

A solution of 4-chloropyridin-2-amine (2.268 g, 17.64 mmol) and NBS (3.14 g, 17.64 mmol) in acetonitrile (176 ml) was stirred at room temperature for 12 h. The solution was diluted with water and extracted with EtOAc (3×100 mL). The combined organics were washed with brine (1×100 mL); dried (MgSO4), filtered and concentrated under reduced pressure to obtain 5-bromo-4-chloropyridin-2-amine (4.28 g, 13.62 mmol, 77% yield) as a pale yellow solid. $^1$H NMR (400 MHz, METHANOL-d4) d 8.04 (s, 1H), 6.74 (s, 1H), LCMS (ESI) m/e 207.0, 209.0 Br pattern [(M+H)$^+$, calcd for $C_5H_5BrClN_2$ 206.9].

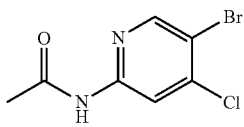

Part C. N-(5-bromo-4-chloropyridin-2-yl)acetamide

To a solution of 5-bromo-4-chloropyridin-2-amine (2.83 g, 13.62 mmol) in pyridine (34.1 ml) at 0° C. was added acetyl chloride (1.07 ml, 14.98 mmol). After complete addition the solution was warmed to room temperature and stirred for 2 h. The excess pyridine was removed under reduced pressure. The residue was diluted with EtOAc (75 mL) and washed with water (2×25 mL). The combined aqueous layers were extracted with EtOAc (2×25 mL). The combined organics were washed with brine (1×20 mL), dried (MgSO4), filtered, and concentrated under reduced pressure. The residue was purified via silica gel chromatography (5%-70% EtOAc in hexanes) to obtain N-(5-bromo-4-chloropyridin-2-yl)acetamide (3.6 g, 12.99 mmol, 95% yield) as a pale yellow-pink solid. $^1$H NMR (400 MHz, CHLOROFORM-d) δ 8.43 (s, 1H), 8.38 (s, 1H), 7.98 (br. s., 1H), 2.23 (s, 3H); LCMS (ESI) m/e 248.9, 250.9 Br pattern [(M+H)$^+$, calcd for $C_7H_7BrClN_2O$ 248.9].

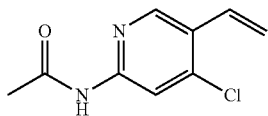

Part D. N-(4-chloro-5-vinylpyridin-2-yl)acetamide

To a sealable vial was added N-(5-bromo-4-chloropyridin-2-yl)acetamide (0.72 g, 2.89 mmol), 2,4,6-trivinylcyclotriboroxane pyridine complex (0.903 g, 3.75 mmol), tetrakis(triphenylphosphine)palladium(0) (0.100 g, 0.087 mmol), and sodium carbonate (0.612 g, 5.77 mmol) followed by toluene (5.18 mL) and EtOH (0.829 mL). The solution was degassed with N$_2$ for 5 min then the vial was heated to 85° C. for 16 h. The mixture was cooled to room temperature and filtered through diatomaceous earth (Celite®) eluting with EtOAc. The solution was concentrated under reduced pressure. The residue was purified via silica gel chromatography (10%-40% EtOAc in hexanes) to obtain N-(4-chloro-5-vinylpyridin-2-yl)acetamide (0.6 g, 1.83 mmol, 60% yield) as a pale yellow-pink solid. $^1$H NMR (400 MHz, CHLOROFORM-d) δ 8.41 (s, 1H), 8.30 (s, 1H), 8.13 (br. s., 1H), 7.01-6.87 (m, 1H), 5.77 (dd, J=17.8, 0.8 Hz, 1H), 5.42 (dd, J=11.2, 0.9 Hz, 1H), 2.23 (s, 3H); LCMS (ESI) m/e 197.1 [(M+H)$^+$, calcd for $C_9H_{10}ClN_2O$ 197.1].

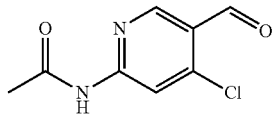

Part E. N-(4-chloro-5-formylpyridin-2-yl)acetamide

To a solution of N-(4-chloro-5-vinylpyridin-2-yl)acetamide (568 mg, 2.89 mmol) and 2,6-lutidine (673 μL, 5.78 mmol) in dioxane (10.2 mL) and water (2.3 mL) cooled to 0° C. was added osmium tetroxide (2.5% in 2-methyl-2-propanol) (588 mg, 0.058 mmol) followed by sodium periodate (2.47 g, 11.56 mmol). The resultant mixture was stirred at 0° C. for 3 h. The reaction was quenched with water (3 mL) and extracted with EtOAc (3×10 mL). The combined organics were washed with brine (1×10 mL), dried (MgSO$_4$), filtered, and concentrated under reduced pressure. The residue was purified via silica gel chromatography (5%-70% EtOAc in hexanes) to obtain N-(4-chloro-5-formylpyridin-2-yl)acetamide (430 mg, 2.057 mmol, 71% yield) as an off-white solid. $^1$H NMR (400 MHz, CHLOROFORM-d) δ 10.38 (s, 1H), 8.76 (s, 1H), 8.40 (s, 1H), 8.33 (br. s., 1H), 2.28 (s, 3H); LCMS (ESI) m/e 199.1 [(M+H)$^+$, calcd for $C_8H_8ClN_2O_2$ 199.1].

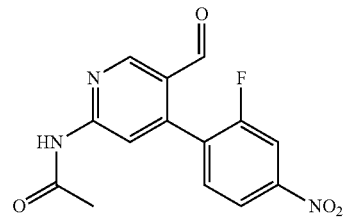 [SMILES: CC(=O)Nc1cc(-c2ccc([N+](=O)[O-])cc2F)c(C=O)cn1]

Part F. N-(4-(2-fluoro-4-nitrophenyl)-5-formylpyridin-2-yl)acetamide

A mixture of N-(4-chloro-5-formylpyridin-2-yl)acetamide (0.3 g, 1.51 mmol), 2-(2-fluoro-4-nitrophenyl)-4,4,5,5-tetramethyl-1,3,2-dioxaborolane (0.576 g, 1.36 mmol) and cesium carbonate (0.984 g, 3.02 mmol) in dioxane (4.83 mL) and water (1.21 mL) was purged with N2 gas for 10 min. Tetrakis(triphenylphosphine)palladium(0) (0.349 g, 0.302 mmol) was added and the mixture was heated to 95° C. for 12 h. The residue was purified via silica gel chromatography (20%-80% EtOAc in hexanes) to obtain N-(4-(2-fluoro-4-nitrophenyl)-5-formylpyridin-2-yl)acetamide (250 mg, 0.742 mmol, 49% yield) as a yellow solid. $^1$H NMR (500 MHz, CHLOROFORM-d) δ 9.90 (d, J=2.0 Hz, 1H), 8.87 (s, 1H), 8.59 (br. s., 1H), 8.31 (s, 1H), 8.20 (ddd, J=8.4, 2.1, 0.6 Hz, 1H), 8.08 (dd, J=9.0, 2.1 Hz, 1H), 7.58 (dd, J=8.3, 7.1 Hz, 1H), 2.30 (s, 3H); LCMS (ESI) m/e 304.1 [(M+H)$^+$, calcd for $C_{14}H_{11}FN_3O_4$ 304.1].

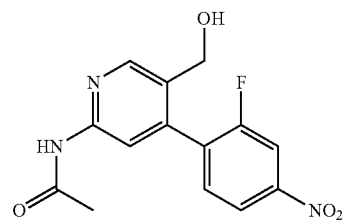 [SMILES: CC(=O)Nc1cc(-c2ccc([N+](=O)[O-])cc2F)c(CO)cn1]

Part G. N-(4-(2-fluoro-4-nitrophenyl)-5-(hydroxymethyl)pyridin-2-yl) acetamide

To a solution of N-(4-(2-fluoro-4-nitrophenyl)-5-formylpyridin-2-yl)acetamide (0.225 g, 0.742 mmol) in tetrahydrofuran (4.57 mL) and methanol (1.14 mL) cooled to 0° C. was added sodium borohydride (0.028 g, 0.742 mmol). The solution was allowed to warm to room temperature and was stirred for 1 h. The reaction was quenched with saturated aqueous sodium bicarbonate (5 mL) and extracted with EtOAc (3×10 mL). The combined organics were washed with brine (1×10 mL), dried (MgSO4), filtered, and concentrated under reduced pressure. The N-(4-(2-fluoro-4-nitrophenyl)-5-(hydroxymethyl)pyridin-2-yl)acetamide so obtained was carried on without further purification. LCMS (ESI) m/e 306.1 [(M+H)$^+$, calcd for $C_{14}H_{13}FN_3O_4$ 306.1].

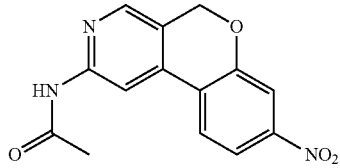

Part H. N-(8-nitro-5H-chromeno[3,4-c]pyridin-2-yl) acetamide

To a solution of N-(4-(2-fluoro-4-nitrophenyl)-5-(hydroxymethyl)pyridin-2-yl)acetamide (0.227 g, 0.742 mmol) in THF (7.42 mL) was added sodium hydride (60 wt % in oil) (0.030 g, 0.742 mmol). The mixture was stirred at room temperature for 10 h. The mixture was quenched with water (5 mL) and extracted with EtOAc (3×10 mL). The combined organics were washed with brine (1×10 mL), dried (MgSO$_4$), filtered, and concentrated under reduced pressure. The residue was purified via silica gel chromatography (5%-100% EtOAc in hexanes) to obtain N-(8-nitro-5H-chromeno[3,4-c]pyridin-2-yl)acetamide (117 mg, 0.390 mmol, 53% yield for two steps) as a pale yellow solid. $^1$H NMR (400 MHz, CHLOROFORM-d) δ 8.61 (m, 1H), 8.17 (br. s., 1H), 7.98 (m, 3H), 7.87 (m, 1H), 5.23 (s, 2H), 2.27 (s, 3H); LCMS (ESI) m/e 286.1 [(M+H)$^+$, calcd for $C_{14}H_{12}N_3O_4$ 286.1].

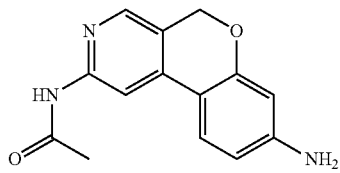 [SMILES: CC(=O)Nc1cc2c(cn1)COc1cc([N+](=O)[O-])ccc1-2]

Part I. N-(8-amino-5H-chromeno[3,4-c]pyridin-2-yl) acetamide

A solution of N-(8-nitro-5H-chromeno[3,4-c]pyridin-2-yl)acetamide (17 mg, 0.060 mmol) and 10% palladium on carbon (6.34 mg, 0.060 mmol) in EtOH was shaken under 40 psi of hydrogen gas for 2 h. The mixture was filtered through diatomaceous earth (Celite®) eluting with EtOAc and concentrated under reduced pressure. The material was carried on without further purification. Obtained N-(8-amino-5H-chromeno[3,4-c]pyridin-2-yl)acetamide (14 mg, 0.044 mmol, 74% yield) as a yellow solid. $^1$H NMR (400 MHz, CHLOROFORM-d) δ 7.97 (s, 1H), 7.57 (d, J=8.5 Hz, 1H), 7.28 (s, 1H), 6.47 (dd, J=8.7, 2.1 Hz, 1H), 6.21 (d, J=2.3 Hz, 1H), 5.07 (s, 2H), 2.29 (s, 3H); LCMS (ESI) m/e 256.1 [(M+H)$^+$, calcd for $C_{14}H_{14}N_3O_2$ 256.1].

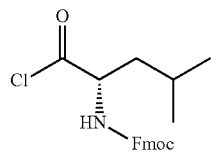

Part J. (S)-(9H-fluoren-9-yl)methyl (1-chloro-4-methyl-1-oxopentan-2-yl)carbamate To a solution of (S)-2-((((9H-fluoren-9-yl)methoxy)carbonyl)amino)-4-methylpentanoic acid (200 mg, 0.566 mmol) in DCM (1132 µL) was added thionyl chloride (2M in DCM) (2830 µL, 5.66 mmol) dropwise followed by DMF (55.0 µL, 0.71 mmol). The mixture was then heated to reflux for 1 h. The solution was then cooled to room temperature and concentrated under reduced pressure. DCM (10 mL) was added to the residue and concentrated under reduced pressure (3×) to remove excess thionyl chloride. The acid chloride was carried on without purification. A small aliquot of the acid chloride was quenched with methanol: LC/MS was consistent with formation of the methyl ester via the acid chloride (methyl ester: LCMS (ESI) m/e 368.8 [(M+H)$^+$, calcd for $C_{22}H_{26}NO_4$ 368.2]).

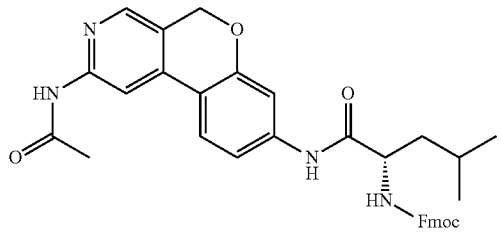

Part K. (S)-(9H-fluoren-9-yl)methyl (1-((2-acetamido-5H-chromeno[3,4-c]pyridin-8-yl)amino)-4-methyl-1-oxopentan-2-yl)carbamate To a solution of N-(8-amino-5H-chromeno[3,4-c]pyridin-2-yl)acetamide (21.44 mg, 0.084 mmol) and DIEA (44.0 µL, 0.252 mmol) in DMF (840 µL) was added a solution of (S)-(9H-fluoren-9-yl)methyl (1-chloro-4-methyl-1-oxopentan-2-yl)carbamate (31.2 mg, 0.084 mmol) in DMF (0.2 mL). The mixture was stirred at room temperature for 12 h. The crude material was purified by reverse phase HPLC (AcCN/H$_2$O/0.1% TFA) to obtain (S)-(9H-fluoren-9-yl)methyl (1-((2-acetamido-5H-chromeno[3,4-c]pyridin-8-yl)amino)-4-methyl-1-oxopentan-2-yl)carbamate (25 mg, 0.038 mmol, 45% yield over two steps) as a yellow solid. $^1$H NMR (400 MHz, CHLOROFORM-d) δ 12.78 (br. s., 1H), 8.78 (s, 1H), 8.65 (br. s., 1H), 7.89 (s, 1H), 7.81-7.72 (m, 3H), 7.58 (d, J=7.8 Hz, 2H), 7.45 (d, J=2.0 Hz, 1H), 7.44-7.39 (m, 2H), 7.37-7.28 (m, 3H), 7.15 (d, J=7.5 Hz, 1H), 5.25 (d, J=6.0 Hz, 1H), 5.09 (s, 2H), 4.52 (d, J=6.3 Hz, 2H), 4.23 (t, J=6.3 Hz, 1H), 2.37 (s, 3H), 1.83-1.56 (m, 3H), 0.99 (d, J=6.3 Hz, 3H), 0.96 (d, J=5.5 Hz, 3H); LCMS (ESI) m/e 591.9 [(M+H)$^+$, calcd for $C_{35}H_{35}N_4O_5$ 591.3].

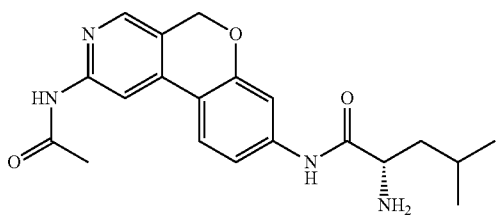 [SMILES: CC(=O)Nc1cc2c(cn1)COc1cc(NC(=O)[C@@H](N)CC(C)C)ccc1-2]

Part L. (S)—N-(2-acetamido-5H-chromeno[3,4-c]pyridin-8-yl)-2-amino-4-methylpentanamide A solution of (S)-(9H-fluoren-9-yl)methyl (1-((2-acetamido-5H-chromeno[3,4-c]pyridin-8-yl)amino)-4-methyl-1-oxopentan-2-yl)carbamate (8.2 mg, 0.014 mmol) and diethylamine (72.5 µL, 0.694 mmol) in acetonitrile (139 µL) was stirred at room temperature for 1.5 h. The solution was concentrated under reduced pressure. The crude material was purified by reverse phase HPLC (AcCN/H2O/0.1% TFA) to obtain (S)—N-(2-acetamido-5H-chromeno[3,4-c]pyridin-8-yl)-2-amino-4-methylpentanamide, 2 TFA (3.5 mg, 5.28 µmol, 38% yield) as a pale yellow film. $^1$H NMR (400 MHz, METHANOL-d4) δ 8.18 (br. s., 1H), 8.04 (br. s., 1H), 7.87 (d, J=8.5 Hz, 1H), 7.52 (d, J=1.8 Hz, 1H), 7.35 (dd, J=8.5, 2.3 Hz, 1H), 5.20 (s, 2H), 4.04 (t, J=7.2 Hz, 1H), 2.28 (br. s., 3H), 1.85-1.73 (m, 3H), 1.05 (d, J=6.3 Hz, 6H); LCMS (ESI) m/e 369.8 [(M+H)$^+$, calcd for $C_{20}H_{25}N_4O_3$ 369.2].

Example 36

(S)-2-amino-N-(5H-chromeno[3,4-c]pyridin-8-yl)-2-phenylacetamide

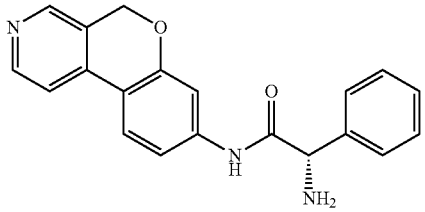 [SMILES: N[C@H](C(=O)Nc1ccc2c(c1)OCc1cnccc1-2)c1ccccc1]

The title compound was prepared following the same protocol described in Example 12 using (S)-2-((tert-butoxycarbonyl)amino)-2-phenylacetic acid (38.0 mg, 0.151 mmol) in Part G to give (S)-2-amino-N-(5H-chromeno[3,4-c]pyridin-8-yl)-2-phenylacetamide, 2 TFA (31.7 mg, 0.056 mmol, 56% yield) as a yellow solid after deprotection. $^1$H NMR (400 MHz, METHANOL-d$_4$) δ 8.80-8.60 (m, 2H), 8.25 (d, J=6.3 Hz, 1H), 8.03 (d, J=8.8 Hz, 1H), 7.68-7.56 (m, 3H), 7.55-7.45 (m, 3H), 7.36 (dd, J=8.7, 2.1 Hz, 1H), 5.35 (s, 2H), 5.17 (s, 1H); LCMS (ESI) m/e 332.1 [(M+H)$^+$, calcd for $C_{20}H_{18}N_3O_2$ 332.1].

Example 37

(S)—N$^1$-(5H-chromeno[3,4-c]pyridin-8-yl)-2-phenylethane-1,2-diamine

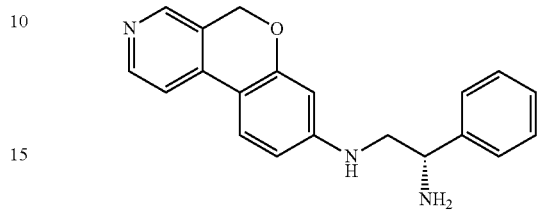

To a solution of (S)-2-amino-N-(5H-chromeno[3,4-c]pyridin-8-yl)-2-phenylacetamide (20 mg, 0.060 mmol), prepared as described in Example 36, in THF was added borane tetrahydrofuran complex (1M in THF) (72.4 µl, 0.072 mmol) dropwise. The solution was heated to 50° C. for 3 h. The reaction was cooled to room temperature, quenched with MeOH (~1 mL) and stirred for 30 min. The solution was concentrated under reduced pressure. The residue was purified by reverse phase HPLC (10%-60% AcCN in H2O/0.1% TFA over 25 min) to obtain (S)—N$^1$-(5H-chromeno[3,4-c]pyridin-8-yl)-2-phenylethane-1,2-diamine, TFA (6 mg, 0.014 mmol, 23% yield) as a yellow oil. $^1$H NMR (400 MHz, METHANOL-d4) d 8.46 (d, J=6.3 Hz, 1H), 8.44 (s, 1H), 8.00 (d, J=6.3 Hz, 1H), 7.81 (d, J=9.0 Hz, 1H), 7.57-7.41 (m, 5H), 6.54 (dd, J=8.8, 2.3 Hz, 1H), 6.31 (d, J=2.3 Hz, 1H), 5.24 (s, 2H), 4.53 (t, J=7.2 Hz, 1H), 3.89-3.77 (m, 1H), 3.75-3.65 (m, 1H); LCMS (ESI) m/e 318.1 [(M+H)$^+$, calcd for $C_{20}H_{20}N_3O$ 318.2].

Methods

AAK1 Kinase Assay

The assays were performed in U-bottom 384-well plates. The final assay volume was 30 µl prepared from 15 µl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 µl of 35 mM EDTA buffer to each sample. The reactions were analyzed on the Caliper LabChip 3000 (Caliper, Hopkinton, Mass.) by electrophoretic separation of the fluorescent substrate and phosphorylated product Inhibition data were calculated by comparison to EDTA quenched control reactions for 100% inhibition and vehicle-only reactions for 0% inhibition. The final concentration of reagents in the assays are ATP, 22 µM; (5-FAM)-Aha-KEEQSQITSQVTGQIGWR-NH2, 1.5 µM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

HEK281 Cell-Based Assay

HEK293F cells were cultured in media containing DMEM (Gibco, cat. #11965). 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 µg Flag/AP2MI/pcDNA (full length human), and 1.5 ml OPTI-MEM. The Lipofectamine 2000 is made up of a mixture (per 10 cm dish) containing 144 µl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% $CO_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 µl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 µl of cell suspension transferred into each well of 96-well TC plate. Finally, 100 µl of 2× compound diluted in DMEM+0.5% FBS was then added into wells containing cell suspension for a 1× final concentration. Plates were then incubated at 37° C. and 5% $CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.#NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 µl per sample was loaded into each lane of a 4-20% Tris-Glycine Criterion 26-well gel (Biorad, cat.#345-0034) for the phospho-mu2 blot and 10 µl per lane in a 4-12% Bis-Tris (+MES buffer) NuPAGE 26-well gel (Invitrogen, cat.#WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.#F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; BioRad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.# RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

The invention claimed is:
1. A compound of formula (I)

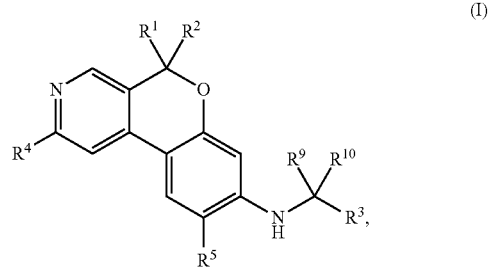

or a pharmaceutically acceptable salt thereof, wherein:
$R^1$ and $R^2$ are independently selected from hydrogen, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or
$R^1$ and $R^2$ together are oxo;
$R^3$ is selected from $C_1$-$C_6$alkoxy, $C_2$-$C_6$alkynyl, amino, $C_3$-$C_6$cycloalkyl optionally substituted with $C_1$-$C_3$alkyl or cyano, $C_3$-$C_6$cycloalkylamino, piperidinyl optionally substituted with $C_1$-$C_6$alkyl, $C_1$-$C_3$alkyl-Y, and $C_1$-$C_8$alkyl, wherein the $C_1$-$C_8$alkyl is optionally substituted with one, two, or three groups independently selected from $C_1$-$C_3$alkoxy, $C_1$-$C_3$alkylamino, $C_1$-$C_3$alkoxy$C_2$-$C_3$alkylamino, $C_1$-$C_3$alkoxycarbonyl, amino, aminosulfonyl, aryl, cyano, $C_1$-$C_3$dialkylamino, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;
$R^4$ is selected from hydrogen, $C_1$-$C_3$alkyl, and $C_1$-$C_3$alkylcarbonylamino;
$R^5$ is selected from hydrogen and $C_1$-$C_3$alkyl;

R$^x$ and R$^y$, together with the nitrogen atom to which they are attached, form a three- to six-member ring optionally substituted with oxo; and Y is selected from

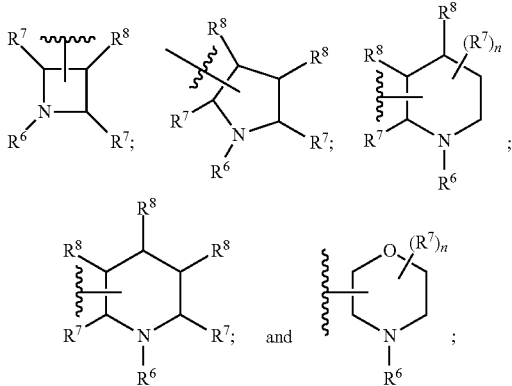

wherein R$^6$ is selected from hydrogen, C$_1$-C$_6$alkyl, C$_3$-C$_6$cycloalkyl, and C$_1$-C$_6$alkylcarbonyl;

n is 0, 1, 2, or 3;

each R$^7$ is independently selected from hydrogen, C$_1$-C$_6$alkyl, aryl, arylC$_1$-C$_3$alkyl, C$_3$-C$_6$cycloalkyl, halo, and C$_1$-C$_3$haloalkyl;

each R$^8$ is independently selected from hydrogen, C$_1$-C$_3$alkoxy and hydroxy; and R$^9$ and R$^{10}$ are each hydrogen or together form an oxo group.

2. A compound of claim 1, or a pharmaceutically acceptable salt thereof, wherein R$^9$ and R$^{10}$ together form an oxo group.

3. A compound of claim 2, or a pharmaceutically acceptable salt thereof, wherein R$^5$ is hydrogen.

4. A compound of claim 3, or a pharmaceutically acceptable salt thereof, wherein R$^4$ is selected from hydrogen and C$_1$-C$_3$ alkylcarbonylamino.

5. A compound of claim 4, or a pharmaceutically acceptable salt thereof, wherein R$^4$ is hydrogen.

6. A compound of claim 2, or a pharmaceutically acceptable salt thereof, wherein R$^3$ is selected from C$_1$-C$_6$alkoxy, C$_2$-C$_6$alkynyl, C$_3$-C$_6$cycloalkyl optionally substituted with cyano, C$_3$-C$_6$cycloalkylamino, piperidinyl optionally substituted with C$_1$-C$_6$alkyl, and C$_1$-C$_8$alkyl, wherein the C$_1$-C$_8$alkyl is optionally substituted with one, group selected from C$_1$-C$_3$alkoxy, C$_1$-C$_3$alkoxycarbonyl, amino, aminosulfonyl, cyano, C$_1$-C$_3$dialkylamino, hydroxy, and —NR$^x$R$^y$; wherein R$^x$ and R$^y$, together with the nitrogen atom to which they are attached, form a five-membered ring optionally substituted with oxo.

7. A compound of claim 2, or a pharmaceutically acceptable salt thereof, wherein:

R$^1$ and R$^2$ are independently selected from hydrogen and C$_1$-C$_3$alkyl, or, R$^1$ and R$^2$ together are oxo;

R$^3$ is selected from C$_1$-C$_6$alkoxy, C$_2$-C$_6$alkynyl, C$_3$-C$_6$cycloalkyl optionally substituted with cyano, C$_3$-C$_6$cycloalkylamino, piperidinyl optionally substituted with C$_1$-C$_6$alkyl, and C$_1$-C$_8$alkyl, wherein the C$_1$-C$_8$alkyl is optionally substituted with one, group selected from C$_1$-C$_3$alkoxy, C$_1$-C$_3$alkoxycarbonyl, amino, aminosulfonyl, cyano, C$_1$-C$_3$dialkylamino, hydroxy, and —NR$^x$R$^y$; wherein R$^x$ and R$^y$, together with the nitrogen atom to which they are attached, form a five-membered ring optionally substituted with oxo;

R$^4$ is selected from hydrogen and C$_1$-C$_3$alkylcarbonylamino; and

R$^5$ is hydrogen.

8. A compound selected from
(R)-2-amino-N-(5H-chromeno[3,4-c]pyridin-8-yl)-4-methylpentanamide;
(S)-2-amino-N-(5H-chromeno[3,4-c]pyridin-8-yl)-4-methylpentanamide;
(S)-2-amino-4-methyl-N—((R)-5-methyl-5H-chromeno[3,4-c]pyridin-8-yl)pentanamide;
(S)-2-amino-4-methyl-N—((S)-5-methyl-5H-chromeno[3,4-c]pyridin-8-yl)pentanamide;
(2R)-2-amino-4-methyl-N-(5-methyl-5H-chromeno[3,4-c]pyridin-8-yl)pentanamide;
(R)-2-amino-4-methyl-N—((R)-5-methyl-5H-chromeno[3,4-c]pyridin-8-yl)pentanamide;
(R)-2-amino-4-methyl-N—((S)-5-methyl-5H-chromeno[3,4-c]pyridin-8-yl)pentanamide;
(R)-2-amino-N-(5,5-dimethyl-5H-chromeno[3,4-c]pyridin-8-yl)-4-methylpentanamide;
(S)-2-amino-N-(5,5-dimethyl-5H-chromeno[3,4-c]pyridin-8-yl)-4-methylpentanamide;
N-(5H-chromeno[3,4-c]pyridin-8-yl)-3-isopropylpiperidine-2-carboxamide;
(S)-2-amino-4-methyl-N-(5-oxo-5H-chromeno[3,4-c]pyridin-8-yl)pentanamide;
neopentyl 5H-chromeno[3,4-c]pyridin-8-ylcarbamate;
1-(5H-chromeno[3,4-c]pyridin-8-yl)-3-cyclohexylurea;
N-(5H-chromeno[3,4-c]pyridin-8-yl)pent-4-ynamide;
N-(5H-chromeno[3,4-c]pyridin-8-yl)pentanamide;
N-(5H-chromeno[3,4-c]pyridin-8-yl)-3-cyanopropanamide;
N-(5H-chromeno[3,4-c]pyridin-8-yl)acetamide;
N-(5H-chromeno[3,4-c]pyridin-8-yl)-3-methoxypropanamide;
N-(5H-chromeno[3,4-c]pyridin-8-yl)-3-hydroxypropanamide;
N-(5H-chromeno[3,4-c]pyridin-8-yl)-1-cyanocyclopropanecarboxamide;
N-(5H-chromeno[3,4-c]pyridin-8-yl)-4-sulfamoylbutanamide;
N-(5H-chromeno[3,4-c]pyridin-8-yl)-3-(2-oxopyrrolidin-1-yl)propanamide;
N-(5H-chromeno[3,4-c]pyridin-8-yl)cyclohexanecarboxamide;
N-(5H-chromeno[3,4-c]pyridin-8-yl)isobutyramide;
N-(5H-chromeno[3,4-c]pyridin-8-yl)-2-cyanoacetamide;
N-(5H-chromeno[3,4-c]pyridin-8-yl)-3,3-dimethylbutanamide;
N-(5H-chromeno[3,4-c]pyridin-8-yl)-3-methylbutanamide;
N-(5H-chromeno[3,4-c]pyridin-8-yl)propionamide;
methyl 4-((5H-chromeno[3,4-c]pyridin-8-yl)amino)-4-oxobutanoate;
N-(5H-chromeno[3,4-c]pyridin-8-yl)-4-methylpentanamide;
N-(5H-chromeno[3,4-c]pyridin-8-yl)butyramide;
N-(5H-chromeno[3,4-c]pyridin-8-yl)pivalamide;
N-(5H-chromeno[3,4-c]pyridin-8-yl)-2-(dimethylamino)acetamide;
N-(9-bromo-5H-chromeno[3,4-c]pyridin-8-yl)pentanamide;
(R)—N-(2-acetamido-5H-chromeno[3,4-c]pyridin-8-yl)-2-amino-4-methylpentanamide;
(S)-2-amino-N-(5H-chromeno[3,4-c]pyridin-8-yl)-2-phenylacetamide; and (S)—N$^1$-(5H-chromeno[3,4-c]pyridin-8-yl)-2-phenylethane-1,2-diamine;
or a pharmaceutically acceptable salt thereof.

9. A composition comprising a pharmaceutically acceptable amount of a compound of claim 1, or a pharmaceutically acceptable salt thereof, and a pharmaceutically acceptable carrier.

10. A method of inhibiting adaptor associated kinase 1 activity, comprising contacting AAK1 with a compound of claim 1, or a pharmaceutically acceptable salt thereof.

\* \* \* \* \*

UNITED STATES PATENT AND TRADEMARK OFFICE
CERTIFICATE OF CORRECTION

PATENT NO. : 9,708,337 B2
APPLICATION NO. : 14/767952
DATED : July 18, 2017
INVENTOR(S) : Vrudhula et al.

Page 1 of 1

It is certified that error appears in the above-identified patent and that said Letters Patent is hereby corrected as shown below:

In the Claims

Claim 1, Column 73, Lines 6-14:

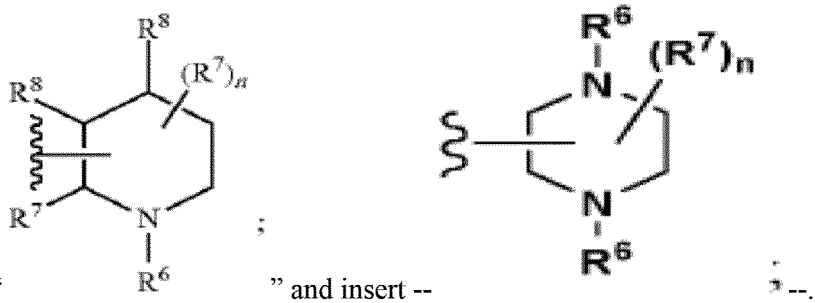

Delete " [structure] " and insert -- [structure] --.

Claim 4, Column 73, Line 40:
Delete "$C_1$-$C_3$ alkylcarbonylamino." and insert -- $C_1$-$C_3$alkylcarbonylamino. --.

Signed and Sealed this
Twenty-seventh Day of November, 2018

Andrei Iancu
*Director of the United States Patent and Trademark Office*